(12) United States Patent
Chang et al.

(10) Patent No.: US 12,383,634 B2
(45) Date of Patent: *Aug. 12, 2025

(54) SINGLE DOMAIN ANTIBODY TARGETING αVβ3 INTEGRIN

(71) Applicant: KOREA BASIC SCIENCE INSTITUTE, Daejeon (KR)

(72) Inventors: Ki-Yuk Chang, Seoul (KR); Kwan-Soo Hong, Cheongju-si (KR); Chan-Woo Kim, Suwon-si (KR); Hyeon-Seung Lee, Daejeon (KR); Hyun-Min Kim, Gimje-si (KR)

(73) Assignee: KOREA BASIC SCIENCE INSTITUTE, Daejeon (KR)

( * ) Notice: Subject to any disclaimer, the term of this patent is extended or adjusted under 35 U.S.C. 154(b) by 1030 days.

This patent is subject to a terminal disclaimer.

(21) Appl. No.: 17/431,357

(22) PCT Filed: Jul. 24, 2019

(86) PCT No.: PCT/KR2019/009144
§ 371 (c)(1),
(2) Date: Aug. 16, 2021

(87) PCT Pub. No.: WO2021/015336
PCT Pub. Date: Jan. 28, 2021

(65) Prior Publication Data
US 2022/0133913 A1 May 5, 2022

(51) Int. Cl.
*A61K 49/00* (2006.01)
*C07K 16/28* (2006.01)
*G01N 33/574* (2006.01)

(52) U.S. Cl.
CPC ...... *A61K 49/0032* (2013.01); *A61K 49/0058* (2013.01); *C07K 16/28* (2013.01); *G01N 33/57492* (2013.01); *G01N 2333/70557* (2013.01)

(58) Field of Classification Search
CPC ............ A61K 49/0032; A61K 49/0058; A61K 2039/505; C07K 16/28; C07K 2317/22; C07K 2317/569; C07K 2317/92; C07K 16/2848; G01N 33/57492; G01N 2333/70557; G01N 2800/7014
See application file for complete search history.

(56) References Cited

U.S. PATENT DOCUMENTS

| | | | |
|---|---|---|---|
| 6,171,588 B1 | 1/2001 | Carron et al. | |
| 6,369,204 B1 | 4/2002 | Kim et al. | |
| 2008/0175840 A1 | 7/2008 | Brooks et al. | |
| 2009/0053238 A1 | 2/2009 | Allan | |

FOREIGN PATENT DOCUMENTS

| | | |
|---|---|---|
| KR | 10-2019-0108308 A | 9/2019 |
| WO | 2018/183894 A1 | 10/2018 |

OTHER PUBLICATIONS

Kim, Chan Woo et al. αvβ3 nanobody-conjugated PLGA nanoparticles for molecular imaging of angiogenesis International Conference on Nanomedicine and Nanobiotechnology, PS1 Poster Session. Sep. 25, 2017.*
Kim et al. (International Conference on Nanomedicine and Nanobiotechnology 2017, PS1 Poster Session., Sep. 25, 2017).*
International Search Report for PCT/KR2019/009144 dated for Apr. 24, 2020.

* cited by examiner

*Primary Examiner* — Alana Harris Dent
(74) *Attorney, Agent, or Firm* — Sughrue Mion, PLLC

(57) ABSTRACT

Disclosed are an $\alpha_v\beta_3$ integrin targeting single-domain antibody and various applications thereof. The $\alpha_v\beta_3$ integrin targeting single-domain antibody exhibits high binding ability to $\alpha_v\beta_3$ integrin related to angiogenesis, excellent tissue permeability, and biostability compared to conventional antibodies. Further, the single-domain antibody may be combined with fluorescent particles and thus may be easily measured in vitro, in vivo or ex vivo, and may be effective in detecting angiogenesis and diagnosing angiogenesis related diseases, therefore it may be usefully used in related industries.

15 Claims, 16 Drawing Sheets

Specification includes a Sequence Listing.

[FIG. 1]
Lane 1-4: the product of the 1st PCR
Lane M: molecular weight standard, DL2000, from Takara
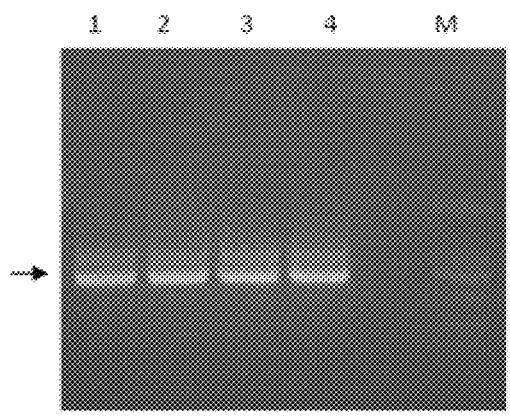
[FIG. 2]
Lane 1-2: the product of the 2nd PCR
Lane M1 and 2, molecular weight standard, DL2000, from Takara
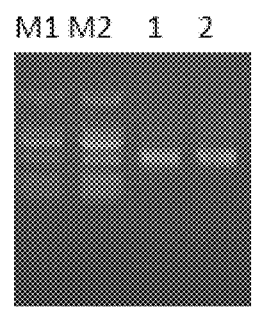

[FIG. 3]
Lane 1-4: cut VHH gene fragments
Lane M: molecular weight standard, DL2000, from Takara
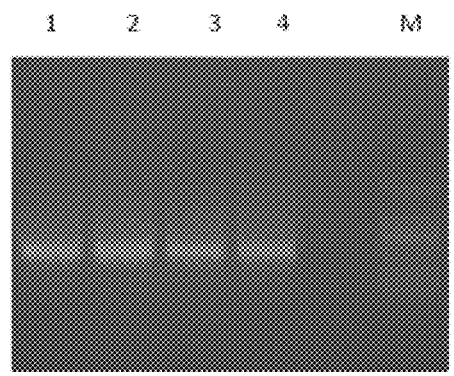
[FIG. 4]
Lane 1-2: Cut phagemids
Lane M: Molecular weight standard, DL2000, from Takara
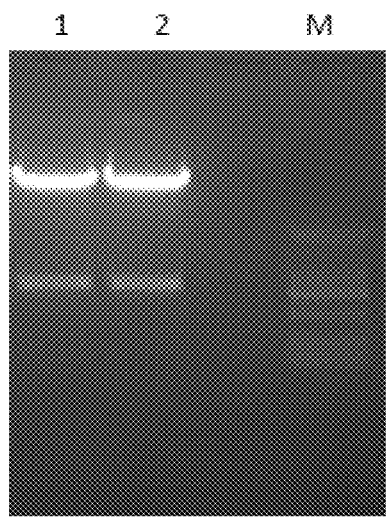

[FIG. 5]

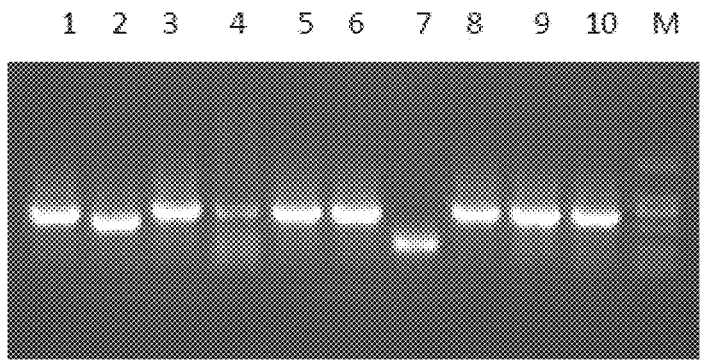

[FIG. 6A]

| | |
|---|---|
| 04092012-VHH-lib-1 | TGAGGAGACAGTGACC... ...G AGT GG |
| 04092012-VHH-lib-2 | TGAGGAGACAGTGACC... -GA ATT T C AC ---- GC |
| 04092012-VHH-lib-3 | TGAGGAGACAGTGACC... - GTGCC C TT CGGAGTGCCG |
| 04092012-VHH-lib-4 | TGAGGAGACAGTGACC... - ACC AAGAC C -GA- G A- |
| 04092012-VHH-lib-5 | TGAGGAGACAGTGACC... -GA ACC AA T AGTG-GG- GAAA |
| 04092012-VHH-lib-6 | TGAGGAGACAGTGACC... -ACACC AA CG T GG- A GG |
| 04092012-VHH-lib-7 | TGAGGAGACAGTGACC... - GG T C AAT CATAG -CCA |
| 04092012-VHH-lib-8 | TGAGGAGACAGTGACC... - ACT AA CT A GG TCG CA |
| 04092012-VHH-lib-9 | TGAGGAGACAGTGACC... - AAC AA TT A G ----C CTG |
| 04092012-VHH-lib-10 | TGAGGAGACAGTGACC... AA GTTCG -GA ACCTG AGAG TG |
| 04092012-VHH-lib-11 | TGAGGAGACAGTGACC... - GGT T CT -- CC ACCG GA |
| 04092012-VHH-lib-12 | TGAGGAGACAGTGACC... - GTTGT A AAT AATAG A T |
| 04092012-VHH-lib-13 | TGAGGAGACAGTGACC... T C TCT CCAAT GCGA G C |
| 04092012-VHH-lib-14 | TGAGGAGACAGTGACC... - GTT -TACTG ---- CCC |
| 04092012-VHH-lib-15 | TGAGGAGACAGTGACC... - TGT TA GGAGA TG-TA T |
| 04092012-VHH-lib-16 | TGAGGAGACAGTGACC... ---G-TCCAT T CC-C CT |
| 04092012-VHH-lib-17 | TGAGGAGACAGTGACC... GCA ATAGG C CAT ACA |
| 04092012-VHH-lib-18 | TGAGGAGACAGTGACC... T-TG- T AGT CCGA- AAA |
| 04092012-VHH-lib-19 | TGAGGAGACAGTGACC... C---G-TA AT A AT-CG TG |
| 04092012-VHH-lib-20 | TGAGGAGACAGTGACC... TGT A G T GA TG-T GA |

[FIG. 6B]

```
04092012-VHH-lib-1    GGCA-CAGGGTCTGGTGAGTAACCACCAC-----TACAGGTCTATCCTC
04092012-VHH-lib-2    GACCCAAGCGGCGGCAGGGCATCCGAAGCTC------------C-ACGC
04092012-VHH-lib-3    AGATGGTA-GCAGTGCC-GATCTGTGATCTCC------------------
04092012-VHH-lib-4    -----GGAGCG--GAGACGAGGCGCCGACTA-------------------
04092012-VHH-lib-5    TCCGGGGCGGCGGACACGACCTGCCACCGATG------------C-GGAG
04092012-VHH-lib-6    GCGGCAGCAGGTACTATGCGGCGGATGCT---------------------
04092012-VHH-lib-7    AGCTGCGAAGCAGCCATAGCGCCAGGATGTA-------------------
04092012-VHH-lib-8    GGACCAGGCGCCGCCTAGGGGACAA-------------------TC
04092012-VHH-lib-9    TGTGGTGATAGTCGCTATCGCGGAGT---------------CCTGGATC
04092012-VHH-lib-10   GTCATCATTGTCTG--TAGAGTGAGTGAAG-----CACGGGGCTCTTGGC
04092012-VHH-lib-11   AATCAGGCCAGACGGCGGGGTCC---------------------------
04092012-VHH-lib-12   CAGTATTGGCGTCTGGATGATGAC----AT----TCGGCTGCCTT-----
04092012-VHH-lib-13   AG---------GTGACATCGTAGAACCCGGT---------T------C---
04092012-VHH-lib-14   CTAT--GGGGTA-ACCAGGCATGA-------------TGTGCATCCG-ATC
04092012-VHH-lib-15   CGC-ACAAGGGAGGACTGCGGAAGG------G----------GT--CC
04092012-VHH-lib-16   G-------GCAGCCCATAGGGTGA--------------------------
04092012-VHH-lib-17   CAAGAGGGTGAACAGCCGTCATGACACCAAGAGCCTGAACAGCCCTCATC
04092012-VHH-lib-18   ATAGAGGGTGAGCAATAGGTGCGCGA----------T----------C---
04092012-VHH-lib-19   GTT---GGAGATACTACGGCGGG--AA-------C---------C------
04092012-VHH-lib-20   AGTTAGGAGGAACCTCCGGTATGAAGC--------GCGAGGGACGC--CC
```

[FIG. 6C]

```
04092012-VHH-lib-1
04092012-VHH-lib-2
04092012-VHH-lib-3
04092012-VHH-lib-4
04092012-VHH-lib-5
04092012-VHH-lib-6
04092012-VHH-lib-7
04092012-VHH-lib-8
04092012-VHH-lib-9
04092012-VHH-lib-10
04092012-VHH-lib-11
04092012-VHH-lib-12
04092012-VHH-lib-13
04092012-VHH-lib-14
04092012-VHH-lib-15
04092012-VHH-lib-16
04092012-VHH-lib-17
04092012-VHH-lib-18
04092012-VHH-lib-19
04092012-VHH-lib-20
```

[FIG. 7]
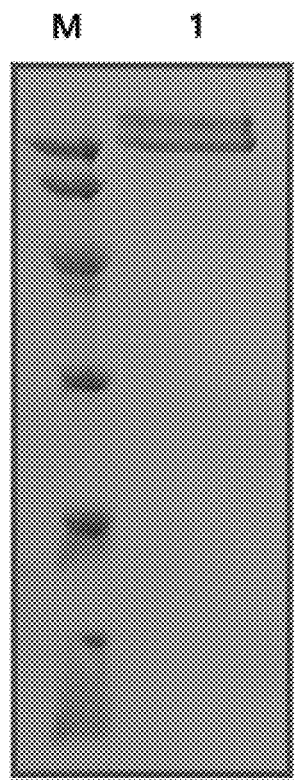

| ID | Sequence |
|---|---|
| 04092012-14 | YCAADRKINCRGIRTTPNANQFTPGQGTLVTVSS |
| 04092012-11 | YCAADRKINCRGIRTTPNANQFTPGQGTLVTVSS |
| 04092012-29 | YCAADPKINCRGIRTTPNADHFNPGQGTLVTVSS |
| 04092012-17 | YCAADPKINCRGIRTTPNADHFNPGQGTLVTVSS |
| 04092012-15 | YCAADRKINCRGIRTTPNANQFTPGQGTQVTVSS |
| 04092012-28 | YCAADRKINCRGIRTTPNANQFTPGQGTQVTVSS |
| 04092012-12 | YCAADRKINCRGIRTTPNANQFTPGQGTQVTVSS |
| 04092012-19 | YCAADRKINCRGIRTTPNANQFTPGQGTQVTVSS |
| 04092012-13 | YCAADRKINCRGIRTTPNANQFTPGQGTQVTVSS |
| 04092012-21 | YCAADRKINCRGIRTTPNANQFTPGQGTQVTVSS |
| 04092012-27 | YCAADRKINCRGIRTTPNANQFTPGQGTQVTVSS |
| 04092012-16 | YCAADTKINCRGIRTTPNANQFNPGQGTQVTVSS |
| 04092012-18 | YCAADTKINCRGIRTTPNANQFNPGQGTQVTVSS |
| 04092012-20 | YCAADTKINCRGIRTTPNAHFNPGQGTLVTVSS |
| 04092012-30 | YCAADTKINCRGIRTTPNAHFNPGQGTLVTVSS |
| 04092012-23 | YCAADRYVYRLVTN----Y-RPSFITGQGTQVTVSS |
| 04092012-24 | YCAADRYVYRLVTN----Y-RPSFITGQGTQVTVSS |
| 04092012-25 | YCHAACYS------------PSRLNGQGTQVTVSS |
| 04092012-22 | YCHAACYS------------PSRLNGQGTLVTVSS |
| 04092012-26 | YCHAACYS------------PSRLNGQGTLVTVSS |

[FIG. 9]
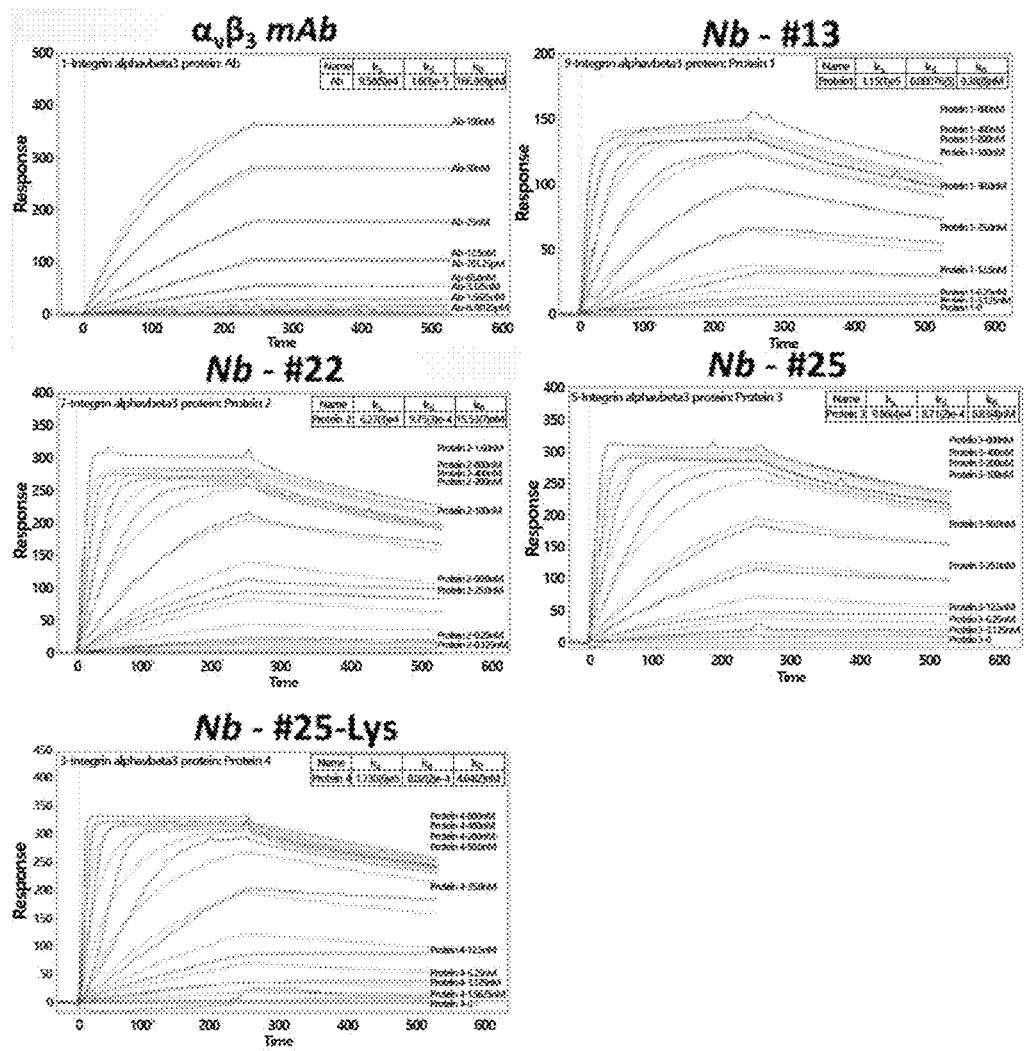

[FIG. 10A]
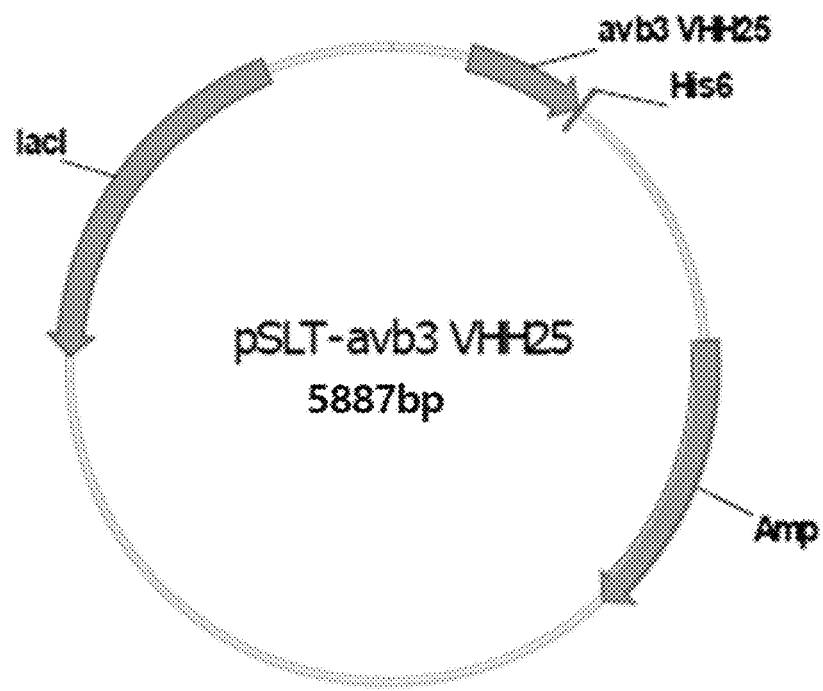
[FIG. 10B]
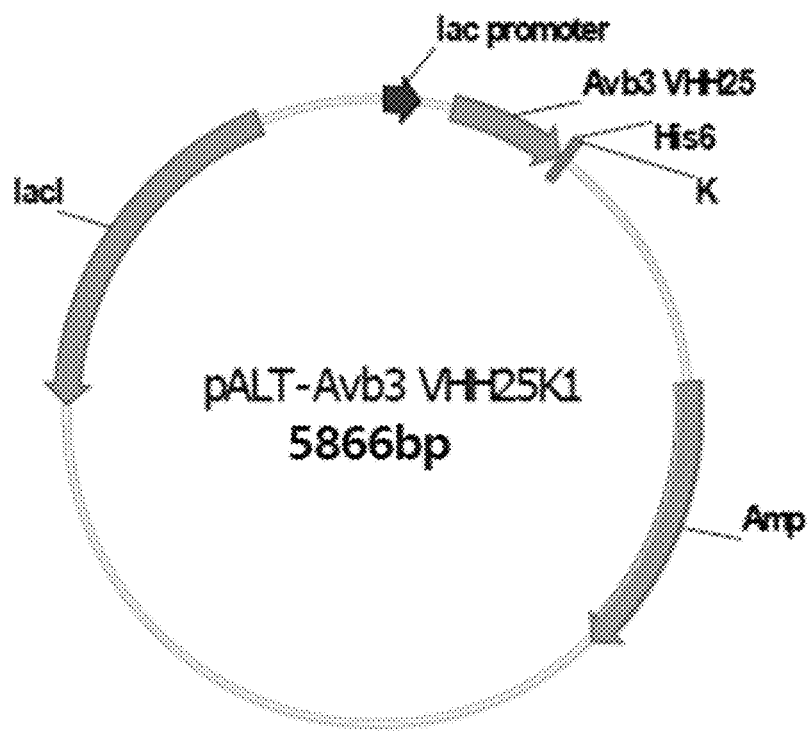

[FIG. 11A]
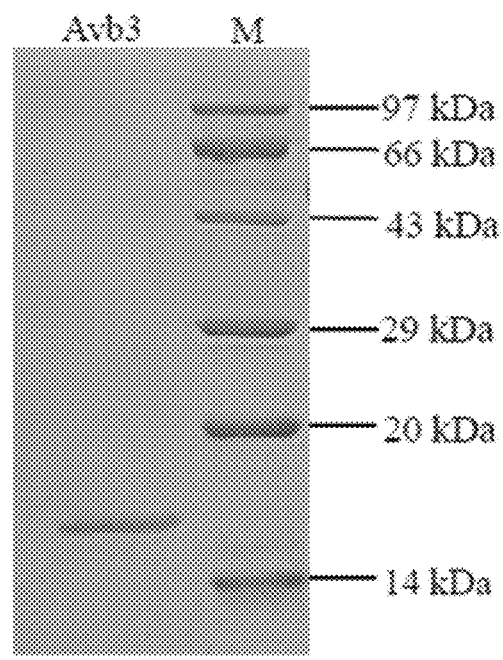
[FIG. 11B]
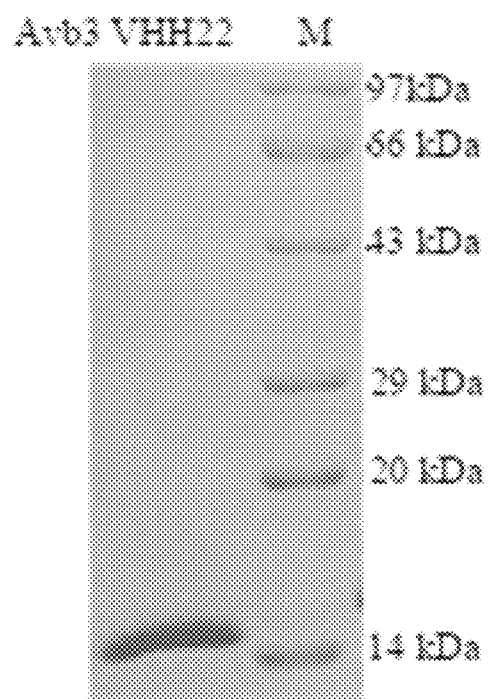

[FIG. 11C]
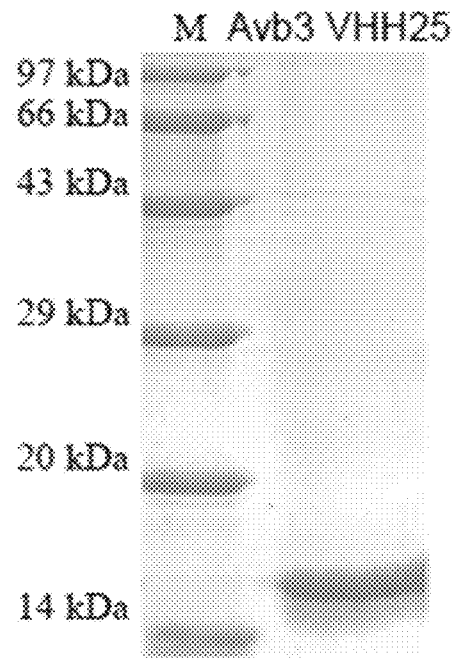
[FIG. 11D]

[FIG. 12]
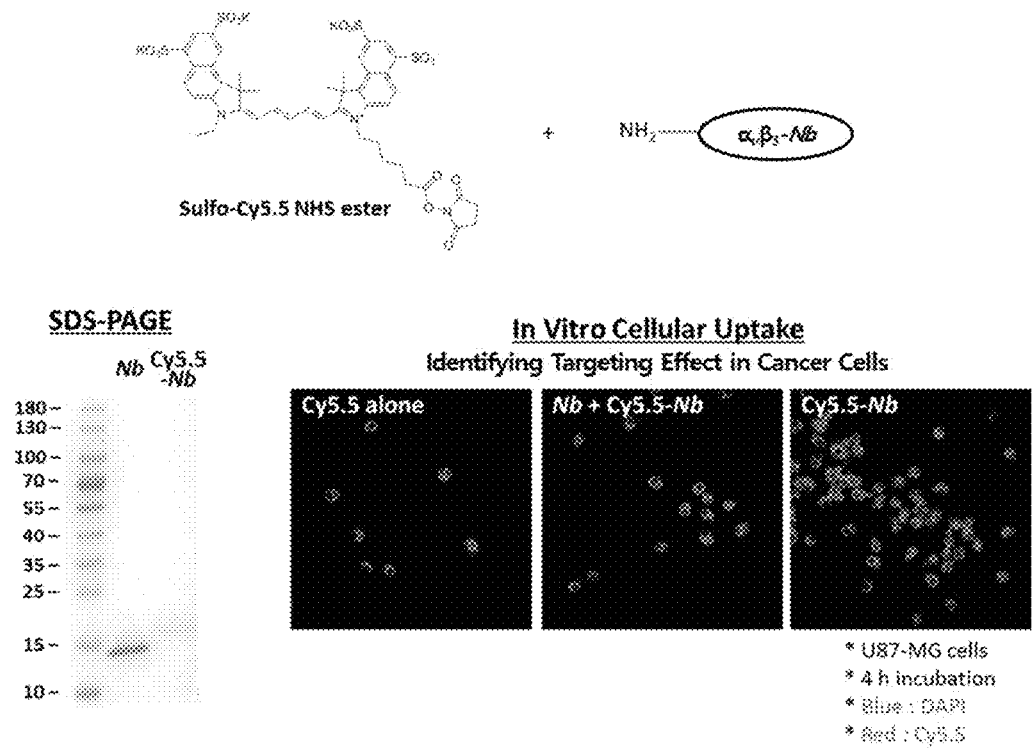
[FIG. 13]
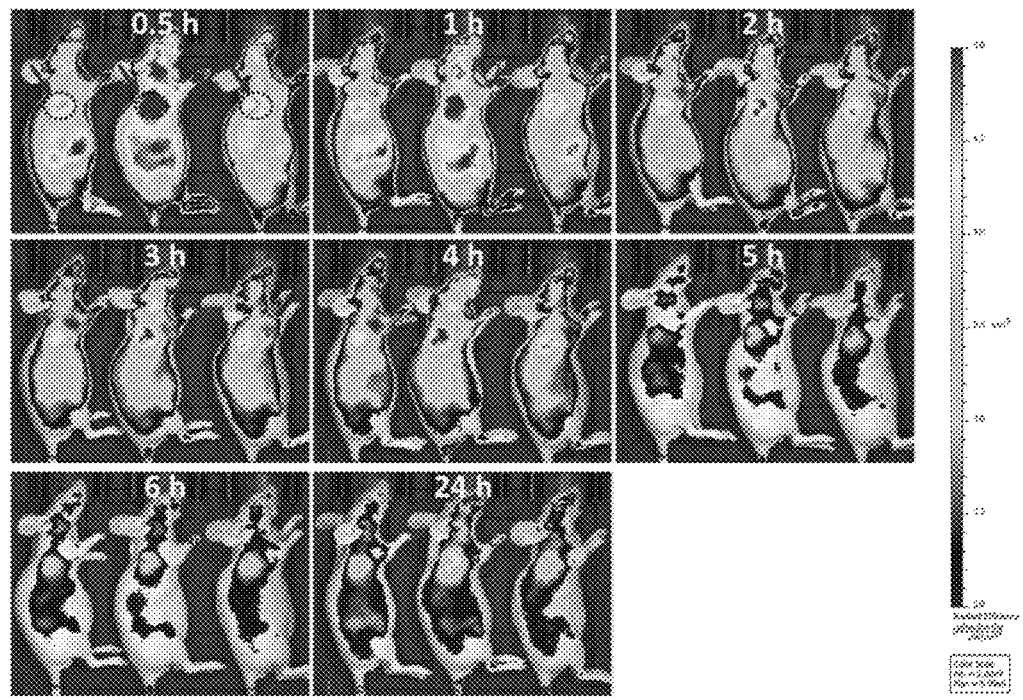

[FIG. 14]
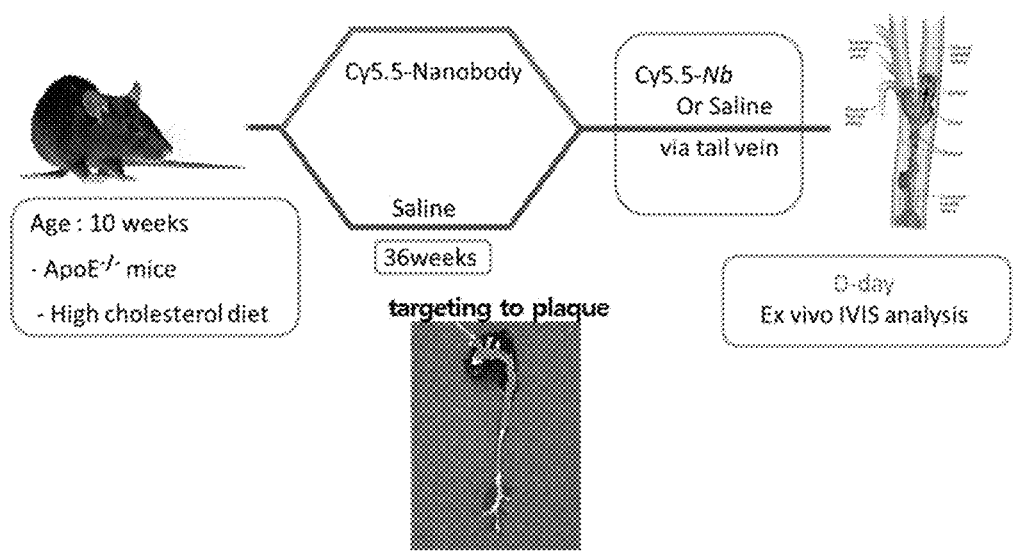

SEQUENCE LISTING

```
<160> NUMBER OF SEQ ID NOS: 16

<210> SEQ ID NO 1
<211> LENGTH: 354
<212> TYPE: DNA
<213> ORGANISM: Artificial Sequence
<220> FEATURE:
<223> OTHER INFORMATION: VHH-25

<400> SEQUENCE: 1
gaggtgcagc tggtggagtc tgggggaggc tcggtgcagg ctggagggtc tctgagactc      60
tcctgtgtag tctctggata cacctgtagc gtctacgaca tgatctggta ccgccagcct     120
ccagggaagg agcgcgagtt cgtctcactc attaatagta atggtagaac aacctacgca     180
gactccgtga agggccgatt caccatctcc caaaacaacg ccaagaacac ggtgtatctg     240
cagatgaaca gcctgaaacc tgaggacacg gcaatgtact actgtcatgc ggcctgctat     300
tcaccctctc ggctgaatta ttggggccag gggacccagg tcactgtctc ctca          354

<210> SEQ ID NO 2
<211> LENGTH: 402
<212> TYPE: DNA
<213> ORGANISM: Artificial Sequence
<220> FEATURE:
<223> OTHER INFORMATION: VHH-13

<400> SEQUENCE: 2
catgtgcagc tggtggagtc tgggggaggc tcggtgcagc ctggagagtc tctgagactc      60
tcctgtgtag cctctggata caccgtcagt agctcctgca tggcctggtt ccgccaggct     120
```

```
ccaggaaagg agcgcgaggt ggtcgcaact attgttgtta ctagtgatac gaccagcact    180
ttctatgccg actccgtaaa gggccgattc accatctccc cagacaacgc caagaataca    240
ctaaatctgc aaatgaatag cctggaaccg tccgacactg ccatgtacta ctgtgcggca    300
gatcgcaagt ggaacgtttg tagtcgtggt tatcgctaca cccctaattg ggccaaccaa    360
tttacgttct ggggccaggg acccaggtc accgtctcct ca                        402
```

<210> SEQ ID NO 3
<211> LENGTH: 354
<212> TYPE: DNA
<213> ORGANISM: Artificial Sequence
<220> FEATURE:
<223> OTHER INFORMATION: VHH-22

<400> SEQUENCE: 3

```
caggtgcagc tggtggagtc tgggggaggc tcggtgcagg ctggagggtc tctgagactc     60
tcctgtgtag tctctggata cacctgtagc gtctacgaca tgatctggta ccgccagcct    120
ccagggaagg agcgcgagtt cgtctcactc attaatagta atggtagaac aacctacgca    180
gactccgtga agggccgatt caccatctcc caaaacaacg ccaagaacac ggtgtatctg    240
cagatgaaca gcctgaaacc tgaggacacg gcaatgtact actgtcatgc ggcctgctat    300
tcaccctctc ggctgaatta ttggggccag gggaccctgg tcaccgtctc ctca          354
```

<210> SEQ ID NO 4
<211> LENGTH: 402
<212> TYPE: DNA
<213> ORGANISM: Artificial Sequence
<220> FEATURE:
<223> OTHER INFORMATION: VHH-11

<400> SEQUENCE: 4

```
gatgtgcagc tggtggagtc tgggggaggc tcggtgcagc tggagagtc tctgagactc      60 tcctgtgtag cctctggata caccgtcagt agctcctgca tggcctggtt ccgccaggct    120
ccaggaaagg agcgcgaggt ggtcgcaact attgttgtta ctagtgatac gaccagcact    180
ttctatgccg actccgtaaa gggccgattc accatctccc cagacaacgc caagaatacg    240
ctaaatctgc aaatgaatag cctggaaccg tccgacactg ccatgtacta ctgtgcggca    300
gatcgcaagt ggaacgtttg tagtcgtggt tatcgctaca cccctaattg ggccaaccaa    360
tttacgttct ggggccaggg gaccttggtc accgtctcct ca                        402
```

<210> SEQ ID NO 5
<211> LENGTH: 402
<212> TYPE: DNA
<213> ORGANISM: Artificial Sequence
<220> FEATURE:
<223> OTHER INFORMATION: VHH-17

<400> SEQUENCE: 5

```
gatgtgcagc tggtggagtc tgggggaggc tcggtgcagc tggagagtc tctgagactc      60 tcctgtgtag cctctggata caccgtcagt agctcctgca tggcctggtt ccgccaggct    120
ccaggaaagg agcgcgaggt ggtcgcaact attgttgtta ctagtgatac gaccagcact    180
ttctatgccg actccgtaaa gggccgattc accatctccc cagacaacgc caagaatacg    240
ctaaatctgc aaatgaatag cctggaaccg tccgacactg ccatgtacta ctgtgcggca    300
gatcgcaagt ggaacgtttg tagtcgtggt tatcgctaca cccctaattg ggccaaccaa    360
```

```
tttacgttct ggggccaggg gaccttggtc accgtctcct ca              402
```

```
<210> SEQ ID NO 6
<211> LENGTH: 402
<212> TYPE: DNA
<213> ORGANISM: Artificial Sequence
<220> FEATURE:
<223> OTHER INFORMATION: VHH-15

<400> SEQUENCE: 6
gaggtgcagc tggtggagtc tgggggaggc tcggtgcagc tggagagtc tctgagactc     60
tcctgtgtag cctctggata caccgtcagt agctcctgca tggcctggtt ccgccaggct   120
ccaggaaagg agcgcgaggt ggtcgcaact attgttgtta ctagtgatac gaccagcact   180
ttctatgccg actccgtaaa gggccgattc accatctccc cagacaacgc caagaatacg   240
ctaaatctgc aaatgaatag cctggaaccg cccgacactg ccatgtacta ctgtgcggca   300
gatcgcaagt ggaacgtttg tagtcgtggt tatcgctaca cccctaattg gccaaccaa   360
tttacgttct ggggccaggg gacccaggtc accgtctcct ca                      402
```

```
<210> SEQ ID NO 7
<211> LENGTH: 402
<212> TYPE: DNA
<213> ORGANISM: Artificial Sequence
<220> FEATURE:
<223> OTHER INFORMATION: VHH-12

<400> SEQUENCE: 7
gaggtgcagc tggtggagtc tgggggaggc tcggtgcagc tggagagtc tctgagactc     60
tcctgtgtag cctctggata caccgtcagt agctcctgca tggcctggtt ccgccaggct   120
ccaggaaagg agcgcgaggt ggtcgcaact attgttgtta ctagtgatac gaccagcact   180
ttctatgccg actccgtaaa gggccgattc accatctccc cagacaacgc caagaatacg   240
ctaaatctgc aaatgaatag cctggaaccg tccgacactg ccatgtacta ctgtgcggca   300
gatcgcaagt ggaacgtttg tagtcgtggt tatcgctaca cccctaattg gccaaccaa   360
tttacgttct ggggccaggg gacccaggtc accgtctcct ca                      402
```

```
<210> SEQ ID NO 8
<211> LENGTH: 399
<212> TYPE: DNA
<213> ORGANISM: Artificial Sequence
<220> FEATURE:
<223> OTHER INFORMATION: VHH-16

<400> SEQUENCE: 8
gatgtgcagc tggtggagtc tgggggaggc tcggtgcagc tggagggtc tctgagactc     60
tcctgtgcag cctctggata caccgtcgag aactcctgca tggcctggtt ccgccaggct   120
ccagggaagg agcgcgaggt ggtcgcaact attgttacta ataatgcgac cggtactttc   180
tatgccgact ccgtgaaggg ccgattcacc gtctcccaag acaacgccaa gaatacgcta   240
aatctgcaaa tgaatagcct ggaacctgag gacacagcca tgtactactg tgcggcagat   300
accaagtgga gtttgtag tcgtggttat cgctacaccc taattgggc caaccaattt     360
aagtactggg gccaggggac ccaggtcacc gtctcctca                          399
```

```
<210> SEQ ID NO 9
<211> LENGTH: 399
<212> TYPE: DNA
<213> ORGANISM: Artificial Sequence
```

<220> FEATURE:
<223> OTHER INFORMATION: VHH-20

<400> SEQUENCE: 9

```
gatgtgcagc tggtggagtc tgggggaggc tcggtgcagc ctggagggtc cctgagactc     60
tcctgtgcag cctctggata caccgtcgat aactcctgca tggcctggtt ccgccaggct    120
ccagggaagg agcgcgaggt ggtcgcaact attgttacta ataatgcgac cagcactttc    180
tatgccgact ccgtgaaggg ccgattcacc gtctcccacg acaacgccaa gaatacgcta    240
aatctgcaaa tgaataccct ggaacctgag gacactgcca tgtactactg tgcggcagat    300
accaagtgga tagtttgtag tcgtggttat cgctacaccc ctaattgggc caaccatttt    360
aattactggg gccaggggac cctggtcacc gtctcctca                           399
```

<210> SEQ ID NO 10
<211> LENGTH: 384
<212> TYPE: DNA
<213> ORGANISM: Artificial Sequence
<220> FEATURE:
<223> OTHER INFORMATION: VHH-23

<400> SEQUENCE: 10

```
catgtgcagc tggtggagtc tgggggaggc tcggtgcaga ctggagggtc tctgagactc     60
tcctgtgcag cctctggata cacctcaagt accgtctaca tggcttggtt ccgccagact    120
ccagggaagc agcgcgaggg ggtcgcagca atttatactg tggtggtcc tacatactat    180
gccgactccg tgaagggccg attcaccatc tcccaagaca acgccaagaa tacggtgtat    240
ctccaaatga acaccctgaa acctgaagac actgccatgt actactgtgc ggccgatcgc    300
tatgtgtacc ggttagttac taactggtac agaccgtctt tttatacata ctggggccag    360
gggacccagg tcaccgtctc ctca                                           384
```

<210> SEQ ID NO 11
<211> LENGTH: 118
<212> TYPE: PRT
<213> ORGANISM: Artificial Sequence
<220> FEATURE:
<223> OTHER INFORMATION: VHH-25 of amino acid

<400> SEQUENCE: 11

```
Glu Val Gln Leu Val Glu Ser Gly Gly Gly Ser Val Gln Ala Gly Gly
1               5                   10                  15

Ser Leu Arg Leu Ser Cys Val Val Ser Gly Tyr Thr Cys Ser Val Tyr
            20                  25                  30

Asp Met Ile Trp Tyr Arg Gln Pro Pro Gly Lys Glu Arg Glu Phe Val
        35                  40                  45

Ser Leu Ile Asn Ser Asn Gly Arg Thr Thr Tyr Ala Asp Ser Val Lys
    50                  55                  60

Gly Arg Phe Thr Ile Ser Gln Asn Asn Ala Lys Asn Thr Val Tyr Leu
65                  70                  75                  80

Gln Met Asn Ser Leu Lys Pro Glu Asp Thr Ala Met Tyr Tyr Cys His
                85                  90                  95

Ala Ala Cys Tyr Ser Pro Ser Arg Leu Asn Tyr Trp Gly Gln Gly Thr
            100                 105                 110

Gln Val Thr Val Ser Ser
        115
```

<210> SEQ ID NO 12

```
<211> LENGTH: 134
<212> TYPE: PRT
<213> ORGANISM: Artificial Sequence
<220> FEATURE:
<223> OTHER INFORMATION: VHH-13 of amino acid

<400> SEQUENCE: 12

His Val Gln Leu Val Glu Ser Gly Gly Gly Ser Val Gln Pro Gly Glu
1               5                   10                  15

Ser Leu Arg Leu Ser Cys Val Ala Ser Gly Tyr Thr Val Ser Ser Ser
            20                  25                  30

Cys Met Ala Trp Phe Arg Gln Ala Pro Gly Lys Glu Arg Glu Val Val
        35                  40                  45

Ala Thr Ile Val Val Thr Ser Asp Thr Thr Ser Thr Phe Tyr Ala Asp
    50                  55                  60

Ser Val Lys Gly Arg Phe Thr Ile Ser Pro Asn Ala Lys Asn Thr
65                  70                  75                  80

Leu Asn Leu Gln Met Asn Ser Leu Glu Pro Ser Asp Thr Ala Met Tyr
                85                  90                  95

Tyr Cys Ala Ala Asp Arg Lys Trp Asn Val Cys Ser Arg Gly Tyr Arg
            100                 105                 110

Tyr Thr Pro Asn Trp Ala Asn Gln Phe Thr Phe Trp Gly Gln Gly Thr
        115                 120                 125

Gln Val Thr Val Ser Ser
    130

<210> SEQ ID NO 13
<211> LENGTH: 118
<212> TYPE: PRT
<213> ORGANISM: Artificial Sequence
<220> FEATURE:
<223> OTHER INFORMATION: VHH-22 of amino acid

<400> SEQUENCE: 13

Gln Val Gln Leu Val Glu Ser Gly Gly Gly Ser Val Gln Ala Gly Gly
1               5                   10                  15

Ser Leu Arg Leu Ser Cys Val Val Ser Gly Tyr Thr Cys Ser Val Tyr
            20                  25                  30

Asp Met Ile Trp Tyr Arg Gln Pro Pro Gly Lys Glu Arg Glu Phe Val
        35                  40                  45

Ser Leu Ile Asn Ser Asn Gly Arg Thr Thr Tyr Ala Asp Ser Val Lys
    50                  55                  60

Gly Arg Phe Thr Ile Ser Gln Asn Asn Ala Lys Asn Thr Val Tyr Leu
65                  70                  75                  80

Gln Met Asn Ser Leu Lys Pro Glu Asp Thr Ala Met Tyr Tyr Cys His
                85                  90                  95

Ala Ala Cys Tyr Ser Pro Ser Arg Leu Asn Tyr Trp Gly Gln Gly Thr
            100                 105                 110

Leu Val Thr Val Ser Ser
        115

<210> SEQ ID NO 14
<211> LENGTH: 126
<212> TYPE: PRT
<213> ORGANISM: Artificial Sequence
<220> FEATURE:
<223> OTHER INFORMATION: VHH-25 with His6 tag for purification

<400> SEQUENCE: 14
```

Glu Val Gln Leu Val Glu Ser Gly Gly Gly Ser Val Gln Ala Gly
1               5                   10                  15

Ser Leu Arg Leu Ser Cys Val Val Ser Gly Tyr Thr Cys Ser Val Tyr
            20                  25                  30

Asp Met Ile Trp Tyr Arg Gln Pro Pro Gly Lys Glu Arg Glu Phe Val
            35                  40                  45

Ser Leu Ile Asn Ser Asn Gly Arg Thr Thr Tyr Ala Asp Ser Val Lys
50                      55                  60

Gly Arg Phe Thr Ile Ser Gln Asn Asn Ala Lys Asn Thr Val Tyr Leu
65                  70                  75                  80

Gln Met Asn Ser Leu Lys Pro Glu Asp Thr Ala Met Tyr Tyr Cys His
            85                  90                  95

Ala Ala Cys Tyr Ser Pro Ser Arg Leu Asn Tyr Trp Gly Gln Gly Thr
            100                 105                 110

Gln Val Thr Val Ser Ser Leu Glu His His His His His His
            115                 120                 125

<210> SEQ ID NO 15
<211> LENGTH: 142
<212> TYPE: PRT
<213> ORGANISM: Artificial Sequence
<220> FEATURE:
<223> OTHER INFORMATION: VHH-13 with His6 tag for purification

<400> SEQUENCE: 15

His Val Gln Leu Val Glu Ser Gly Gly Gly Ser Val Gln Pro Gly Glu
1               5                   10                  15

Ser Leu Arg Leu Ser Cys Val Ala Ser Gly Tyr Thr Val Ser Ser Ser
            20                  25                  30

Cys Met Ala Trp Phe Arg Gln Ala Pro Gly Lys Glu Arg Glu Val Val
            35                  40                  45

Ala Thr Ile Val Val Thr Ser Asp Thr Thr Ser Thr Phe Tyr Ala Asp
            50                  55                  60

Ser Val Lys Gly Arg Phe Thr Ile Ser Pro Asp Asn Ala Lys Asn Thr
65                  70                  75                  80

Leu Asn Leu Gln Met Asn Ser Leu Glu Pro Ser Asp Thr Ala Met Tyr
            85                  90                  95

Tyr Cys Ala Ala Asp Arg Lys Trp Asn Val Cys Ser Arg Gly Tyr Arg
            100                 105                 110

Tyr Thr Pro Asn Trp Ala Asn Gln Phe Thr Phe Trp Gly Gln Gly Thr
            115                 120                 125

Gln Val Thr Val Ser Ser Leu Glu His His His His His His
            130                 135                 140

<210> SEQ ID NO 16
<211> LENGTH: 126
<212> TYPE: PRT
<213> ORGANISM: Artificial Sequence
<220> FEATURE:
<223> OTHER INFORMATION: VHH-16 with His6 tag for purification

<400> SEQUENCE: 16

Gln Val Gln Leu Val Glu Ser Gly Gly Gly Ser Val Gln Ala Gly Gly
1               5                   10                  15

Ser Leu Arg Leu Ser Cys Val Val Ser Gly Tyr Thr Cys Ser Val Tyr
            20                  25                  30

Asp Met Ile Trp Tyr Arg Gln Pro Pro Gly Lys Glu Arg Glu Phe Val
            35                  40                  45

```
Ser Leu Ile Asn Ser Asn Gly Arg Thr Thr Tyr Ala Asp Ser Val Lys
    50              55                  60
Gly Arg Phe Thr Ile Ser Gln Asn Asn Ala Lys Asn Thr Val Tyr Leu
 65              70                  75                      80
Gln Met Asn Ser Leu Lys Pro Glu Asp Thr Ala Met Tyr Tyr Cys His
                 85              90                      95
Ala Ala Cys Tyr Ser Pro Ser Arg Leu Asn Tyr Trp Gly Gln Gly Thr
            100             105                     110
Leu Val Thr Val Ser Ser Leu Glu His His His His His His
        115             120                 125
```

SINGLE DOMAIN ANTIBODY TARGETING αVβ3 INTEGRIN

This application is a National Stage of International Application No. PCT/KR2019/009144 filed Jul. 24, 2019, the entire disclosure of which is incorporated herein by reference.

TECHNICAL FIELD

The present disclosure relates to an $\alpha_v\beta_3$ integrin targeting single-domain antibody and various applications thereof.

BACKGROUND ART

Integrin is a cell surface receptor that regulates important physiological functions of cells such as cell adhesion and migration, differentiation, and proliferation. The integrin acts as a heterodimer in which α and β subunits have non-covalent bonds, and the α and ρ subunits are paired to form 22 integrin families. Integrin mainly binds to extracellular matrix proteins such as vitronectin, fibronectin, collagen, laminin, vWF, and fibrinogen. However, different types of integrins have different specificities to ligands. One type of integrin may bind to several ligands simultaneously. Among them, integrin $\alpha_v\beta_3$ is expressed in most of the aggressive tumor cells among various cancers including skin cancer, prostate cancer, breast cancer, cervical cancer, colon cancer, lung cancer, gallbladder cancer, pancreatic cancer, and stomach cancer. The integrin $\alpha_v\beta_3$ is known to regulate adhesion-dependent tumor cell growth, survival and invasion to improve the malignancy of various human tumors. Recently, it has been shown that β integrin regulates intracellular signaling to act as a mediator independent of adhesion to increase tumor growth and metastasis (David A Cheresh et al., Nature Medicine 2009, 15 (10): 1163). Further, the $\alpha_v\beta_3$ integrin is highly expressed during neovascularization.

Angiogenesis means creation of new capillary vessels from existing blood vessels. Angiogenesis is a strictly controlled phenomenon that rarely occurs under normal physiological conditions, or occurs when the embryo develops during the development of the fertilized egg, when the wound is healed in adults, and during changes in the reproductive system in the female reproductive cycle. In adults, capillary endothelial cells do not divide relatively well, and the rate of division is usually several months to several years. Angiogenesis occurs in a complex process via the interaction of various types of cells with water-soluble factors and extracellular matrix components, and its mechanism of action has not been fully identified. The angiogenesis is responsible for several diseases.

Currently, the number of commercially available antibodies are reported to be 300,000 or more, but most of commercially available antibodies may only be observed in immobilized cells. Thus, it was not possible to observe the folding of proteins or interactions between proteins in the cell in real time. Further, the existing antibodies were too large or chemically unstable to be useful in living cells. However, antibodies derived from camelid by Hamers-Casterman in 1993 consist of only the heavy chain. This structure different from a structure of the conventional antibodies (two heavy chains and two light chains). A single-domain antibody serving as a functionally complete antibody has been reported (Hamers-Casterman. C. et al. 1993. Nature 363:446-448). Existing antibodies have a size of 150 kDa, recombinant antibodies have a size of 25 kDa to 50 kDa. However, single-domain antibodies derived from camels, llamas, and sharks have a size of 12 kDa to 13 kDa. and thus are the smallest antibody, and thus may easily migrate into cells (Cortez-Retamozo. V. et al. al. 2004. Cancer Res. 64:2853-2857). The single-domain antibodies derived from camels, llamas, and sharks have the advantage of being easily expressed in bacteria and yeast due to its easy genetic manipulation (Arbabi-Ghahroudii, M. et al. 1997. FEBS Lett. 414:521-526). Further, the single-domain antibody is highly water-soluble and stable even under extreme pH conditions and temperature conditions up to 90° C. (Dumoulin, M. et al. 2002. Protein Sciii. 11:500-515, Dumoulin, M. et al. 2003. Nature 424:783-788).

DISCLOSURE

Technical Purpose

A purpose of the present disclosure may provide an $\alpha_v\beta_3$ integrin targeting single-domain antibody.

Further, a purpose of the present disclosure may provide a recombinant vector containing at least one selected from the group consisting of base sequences represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

Further, a purpose of the present disclosure may provide a recombinant microorganism transformed with the recombinant vector.

Further, a purpose of the present disclosure may provide a composition for detecting angiogenesis.

Further, a purpose of the present disclosure may provide a kit for detecting angiogenesis.

Further, a purpose of the present disclosure may provide a composition for diagnosing angiogenesis-related diseases, the composition includes the single-domain antibody.

Further, a purpose of the present disclosure may provide a preparation method of an $\alpha_v\beta_3$ integrin targeting single-domain antibody.

Further, a purpose of the present disclosure may provide a method for screening an angiogenesis inhibitor or promoter.

Further, a purpose of the present disclosure may provide a method for providing information for diagnosis of angiogenesis-related disease.

Technical Solution

In order to achieve the purposes, the present disclosure provides an $\alpha_v\beta_{33}$ integrin targeting single-domain antibody encoded by at least one selected from the group consisting of base sequences represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

Further, the present disclosure provides a recombinant vector containing at least one selected from the group consisting of base sequences represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

Further, the present disclosure provides a recombinant microorganism transformed with the recombinant vector.

Further, the present disclosure provides a composition for detecting angiogenesis, the composition including the single-domain antibody.

Further, the present disclosure provides a kit for detecting angiogenesis, the kit including the single-domain antibody.

Further, the present disclosure provides a composition for diagnosing angiogenesis-related diseases, the composition includes the single-domain antibody.

Further, the present disclosure provides a preparation method of an $\alpha_v\beta_3$ integrin targeting single-domain antibody, the method including: (1) culturing a recombinant microorganism transformed with a recombinant vector containing at least one selected from the group consisting of base sequences represented by SEQ ID NO: 1, SEQ ID NO: 2, SEQ ID NO: 3, SEQ ID NO: 4, SEQ ID NO: 5, SEQ ID NO: 6, SEQ ID NO: 7 SEQ ID NO: 8, SEQ ID NO: 9 and SEQ ID NO: 10; and (2) expressing a single-domain antibody for $\alpha_v\beta_3$ integrin in the microorganism.

Further, the present disclosure provides a method for screening an angiogenesis inhibitor or promoter, the method comprising (1) treating a biological sample isolated from a specimen or an animal model with candidate drugs to be analyzed; (2) binding the $\alpha_v\beta_3$ integrin targeting single-domain antibody to the sample and measuring a level of $\alpha_v\beta_3$ integrin protein; and (3) selecting a candidate drug by which the protein level of the (2) is suppressed or enhanced compared to a control.

Further, the present disclosure provides a method for providing information for diagnosis of angiogenesis-related diseases, the method including (a) binding the $\alpha_v\beta_3$ integrin targeting single-domain antibody to a biological sample isolated from a specimen and measuring a level of $\alpha_v\beta_3$ integrin protein; and (b) comparing the level of the $\alpha_v\beta_3$ integrin protein with a reference value obtained from a control sample.

Advantageous Effects

The $\alpha_v\beta_3$ integrin targeting single-domain antibody according to the present disclosure exhibits high binding ability to $\alpha_v\beta_3$ integrin related to angiogenesis, excellent tissue permeability, and biostability compared to conventional antibodies. Further, the single-domain antibody according to the present disclosure may be combined with fluorescent particles and thus may be easily measured in vitro, in vivo or ex vivo, and may be effective in detecting angiogenesis and diagnosing angiogenesis related diseases, therefore it may be usefully used in related industries.

DESCRIPTION OF DRAWINGS

FIG. 1 is a diagram showing the result of performing first PCR amplification to amplify the single-domain antibody expression cassette according to the present disclosure.

FIG. 2 is a diagram showing the results of second PCR amplification to amplify the single-domain antibody expression cassette according to the present disclosure.

FIG. 3 is a diagram showing a fragment of a truncated single domain gene.

FIG. 4 is a diagram identifying a fragment of a truncated phagemid.

FIG. 5 is a diagram showing the result of identifying whether a single-domain antibody clone according to the present disclosure has been inserted into a gene.

Figures 6D, 6E:
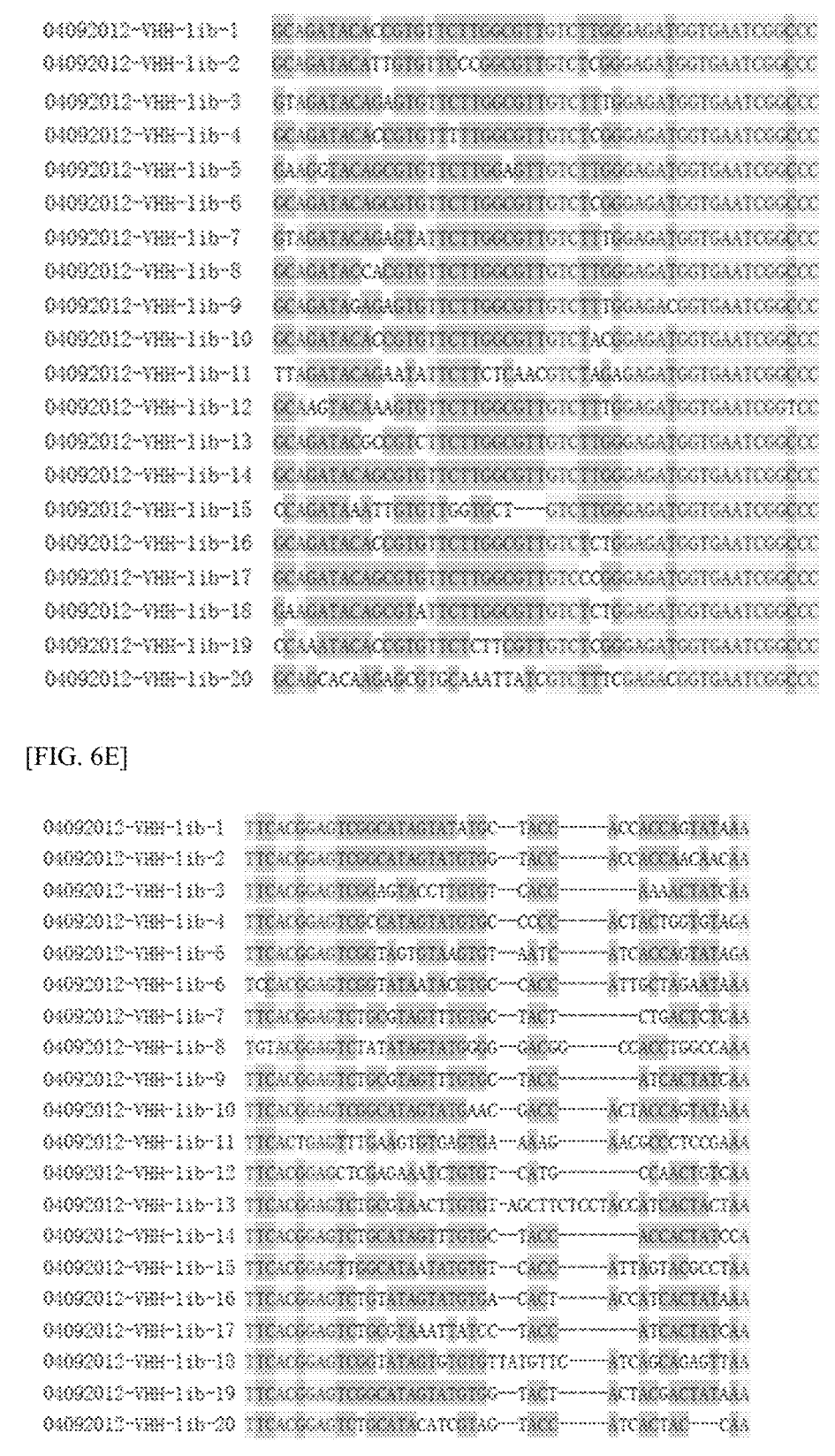
Figures 6F, 6G:
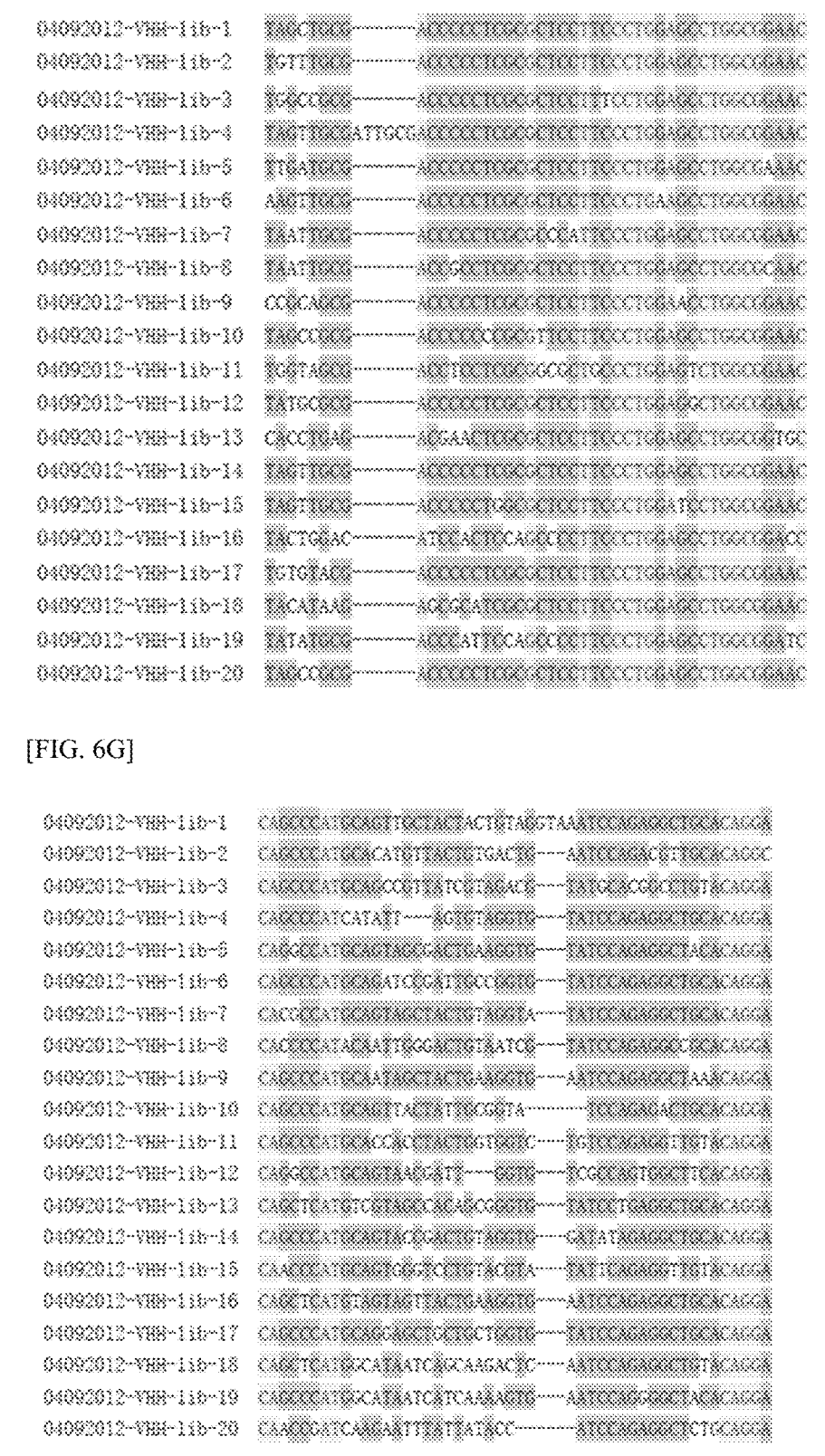

FIG. 6A to FIG. 6I are diagrams showing the results of DNA sequencing of 20 single-domain antibody clones, and alignment results thereof.

FIG. 7 is a diagram showing the SDS-PAGE result of $\alpha_v\beta_3$ integrin protein used to identify $\alpha_v\beta_3$ integrin targeting efficacy according to the present disclosure.

FIG. 8A to FIG. 8C are diagrams showing amino acid sequences of clones exhibiting strong positivity after ELISA is performed.

FIG. 9 is a diagram showing the results of SPR (Surface Plasmon Resonance) analysis of VHH-13, VHH-22 and VHH-25 among single-domain antibody clones.

FIG. 10A is a diagram showing the expression vector map (pALT-Avb3 VHH25) of the single-domain antibody VHH-25 containing His6 tag.

FIG. 10B is a diagram showing the expression vector map (pALT-Avb3 VHH25K1) of the single-domain antibody VHH-25 containing lysin and His6 tag.

FIG. 11A is a diagram showing the result of reduced SDS-PAGE of the single-domain antibody VHH-13 containing His6 tag.

FIG. 11B is a diagram showing the result of reduced SDS-PAGE of the single-domain antibody VHH-22 containing His6 tag.

FIG. 11C is a diagram showing the result of reduced SDS-PAGE of the single-domain antibody VHH-25 containing His6 tag.

FIG. 11D is a diagram showing the result of reduced SDS-PAGE of the single-domain antibody VHH-25 containing lysin and His6 tags.

FIG. 12 is a diagram showing the results of identifying the $\alpha_v\beta_3$ integrin targeting effect of the single-domain antibody VHH-25 according to the present disclosure in cancer cells.

FIG. 13 is a diagram showing the result of identifying the $\alpha_v\beta_3$ integrin targeting effect of the single-domain antibody VHH-25 according to the present disclosure at the tumor site.

FIG. 14 is a diagram showing the result of identifying the $\alpha_v\beta_3$ integrin targeting effect of the single-domain antibody VHH-25 according to the present disclosure at the atherosclerosis site.

MODES OF THE INVENTION

The present disclosure provides an $\alpha_v\beta_3$ integrin targeting single-domain antibody encoded by at least one selected from the group consisting of base sequences represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

The term "$\alpha_v\beta_3$ integrin" in the present disclosure refers to a receptor molecule that exists on the cell surface and acts when cells adhere to extracellular matrix such as fibronectin and collagen. The integrin refers to a transmembrane glycoprotein composed of heterodimers of two subunits, that is, $\alpha$ and $\beta$ subunits. The existence of 21 types of integrins has been revealed so far. Among them, $\alpha_v\beta_3$ integrin has been reported to play a very important role in maintaining the structure of the cardiovascular system and bone tissue.

The term "single-domain antibody" in the present disclosure refers to an antibody in which a CDR is a portion of a single domain polypeptide, and includes heavy chain antibodies, antibodies naturally devoid of light chains, single-domain antibodies derived from conventional 4-chain antibodies, engineered antibodies and single domain scaffolds other than those derived from antibodies. In order to distinguish the single-domain antibody from the VH of the 4-chain immunoglobulin, the single-domain antibody is referred to as a variable region of a heavy chain antibody (VHH), a nanobody, or an sdAb.

The single-domain antibody according to the present disclosure refers to a naturally occurring single-domain antibody derived from a heavy chain naturally free of a light chain, and acts as a specific antibody to $\alpha_v\beta_3$ integrin, and has a molecular weight of about 14 KDa to 15 KDa. The single-domain antibody according to the present disclosure is an antibody that is a VHH derived from Camelidae, and may be derived from camels, dromedaries, llama, alpaca and wild llama. To achieve the goal of targeting $\alpha_v\beta_3$ integrin related to angiogenesis, species other than Camellidae may naturally produce the single-domain antibody as heavy chain antibodies without light chains. However, the present disclosure is not limited thereto.

The single-domain antibody according to the present disclosure is about 10 times smaller than an IgG molecule and is very stable as single polypeptides and are stable under extreme pH and temperature conditions. Further, the single-domain antibody is resistant to the action of proteases, unlike conventional antibodies. When expressed in vitro, mass production of the single-domain antibody may be realized at a high yield.

The base sequence represented by SEQ ID NO: 1 encodes the amino acid sequence of the single-domain antibody represented by SEQ ID NO: 11. The base sequence represented by SEQ ID NO: 2 encodes the amino acid sequence thereof represented by SEQ ID NO: 12. The base sequence represented by SEQ ID NO: 3 may encode the amino acid sequence thereof represented by SEQ ID NO: 13. Further, the amino acid sequences containing the His6 tag in SEQ ID NOs: 1, 2 or 3 may be represented by amino acids of SEQ ID NOs: 14, 15 and 16, respectively.

In one example according to the present disclosure, camels were immunized by injecting, thereto, recombinant $\alpha_v\beta_3$ integrin with cross reactivity in mouse and human, as a targeting protein. Subsequently, mRNA was separated and purified from peripheral lymphocytes isolated from camel blood to synthesize cDNA. After amplifying the variable domains (VHH) of the heavy chain-only antibody by PCR, the VHH was cloned into the M13 bacteriophage gene. Phage display using immobilized immunogen (phosphatidylserine) was performed to select phage clones that react specifically to immobilized antigens.

Figures 8A, 8B:
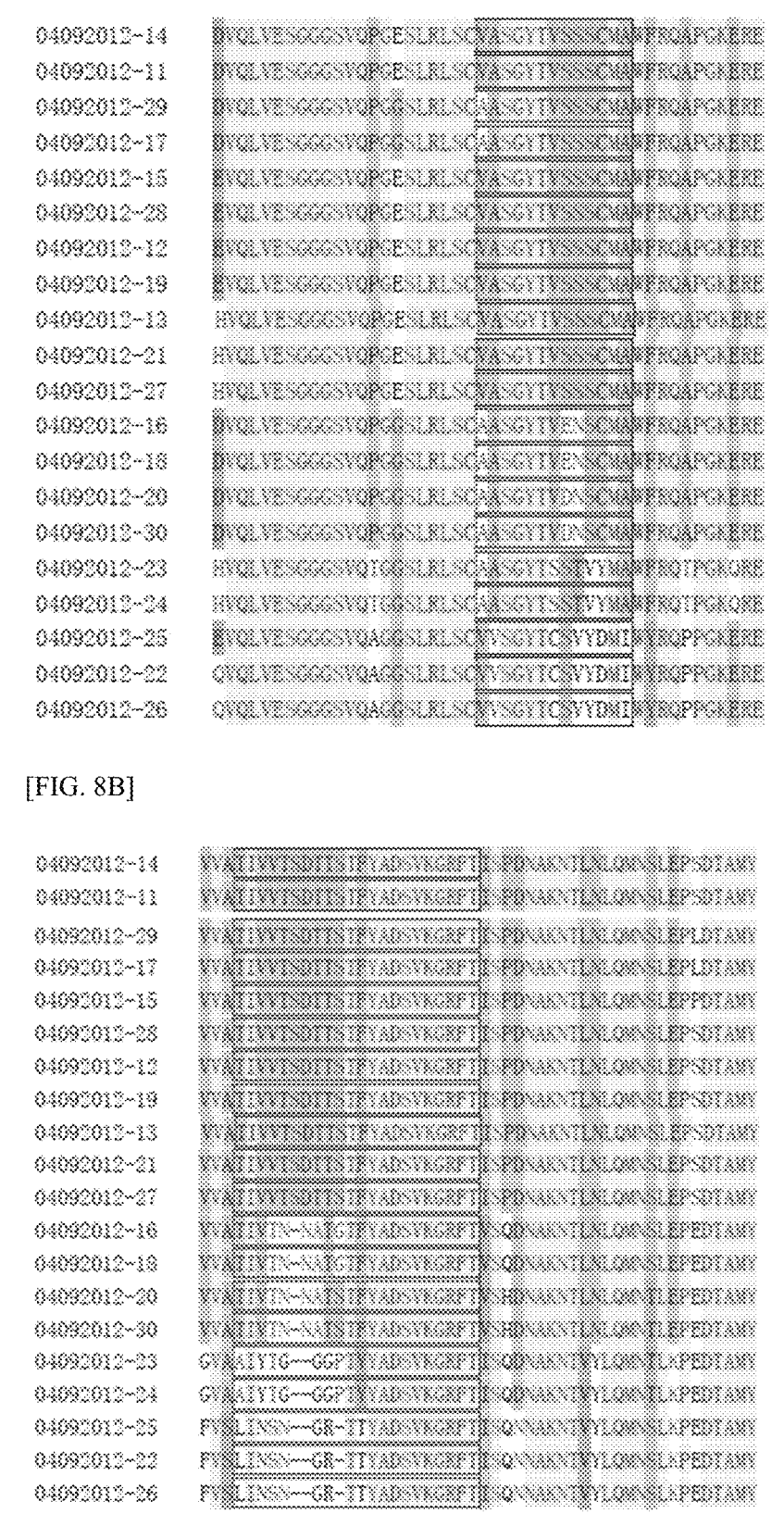

As a result of analyzing the sequence of 40 clones among the phage clones, DNA sequences of 10 candidate groups were identified. Among them, 20 DNA sequences are shown in FIG. 6A to FIG. 6I. Among them, clones 14, 11, 29, 17, 15, 28, 12, 19, 13, 21, 27, 16, 18, 20, 30, 23, 24, 25, 22, and 26 showing high responses in 10 groups were selected, and their amino acid sequences are shown in FIG. 8A to FIG. 8C. Base sequence of the clones VHH-25, VHH-13, VHH-22, VHH-11, VHH-17, VHH-15, VHH-12, VHH-16, VHH-20, and VHH-23 exhibiting strong positives were respectively represented by SEQ ID NOs: 1 to 10. Among them, the amino acid sequences of VHH-25, VHH-13, and VHH-22 are represented by SEQ ID NOs: 11, 12, and 13, respectively.

Variants of the base sequence are included within the scope of the present disclosure. Nucleic acid molecules that may be used as genes encoding proteins constituting a single-domain antibody according to the present disclosure includes functional equivalents of nucleic acid molecules constituting the same, for example, variants in which some base sequences of nucleic acid molecules have been modified by deletion, substitution or insertion, but may function functionally identically to nucleic acid molecules. Specifically, the gene may include a base sequence having a sequence homology of at least 70%, more preferably at least 80%, even more preferably at least 90%, most preferably at least 95% to the nucleotide sequence according to the present disclosure. "% of sequence homology" for a polynucleotide is identified by comparing two optimally arranged sequences with a comparison region. A portion of the polynucleotide sequence in the comparison region may contain additions or deletions (that is, gaps) compared to the reference sequence (not containing additions or deletions) for the optimal arrangement of the two sequences.

The single-domain antibody according to the present disclosure may contain a variant of the amino acid sequence as described in the attached sequence list as long as the variant may specifically recognize $\alpha_v\beta_3$ integrin. For example, modifications may be made to the amino acid sequence of an antibody to alleviate its binding affinity and/or other biological properties. Such modifications include, for example, deletions, insertions and/or substitutions of amino acid sequence residues of the antibody.

The amino acid variation is performed based on the relative similarity of amino acid side chain substituents, such as hydrophobicity, hydrophilicity, charge, size, etc. Based on analysis of the size, shape and type of amino acid side chain substituents, it may be identified that arginine, lysine and histidine are all positively charged residues; alanine, glycine and serine have similar sizes; and phenylalanine, tryptophan and tyrosine have similar shapes. Thus, based on these considerations, arginine, lysine and histidine; alanine, glycine and serine; and phenylalanine, tryptophan, and tyrosine are biologically functional equivalents.

In introducing the variation, the hydropathic index of the amino acid may be considered. Each amino acid is assigned a hydropathic index according to its hydrophobicity and charge: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydropathic amino acid index is very important in imparting an interactive biological function of a protein. It is a known fact that a similar biological activity may be achieved only by substitution with an amino acid having a similar hydropathic index. When introducing the variation with reference to the hydropathic index, substitutions are made between amino acids showing a difference in the hydropathic index, preferably within ±2, more preferably within ±1, and even more preferably within ±0.5.

Further, it is well known that substitutions between amino acids having similar hydrophilicity values result in proteins with equivalent biological activity. As disclosed in U.S. Pat. No. 4,554,101, following hydrophilicity values are assigned to the amino acid residues: arginine (+3.0); lysine (+3.0); aspartate (+3.0 f 1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

When introducing the variation with reference to a hydrophilicity value, substitution may be made between amino acids showing a difference in hydrophilicity values of preferably within ±2, more preferably within ±1, and even more preferably within ±0.5.

Amino acid exchanges in proteins in which the activity of the molecule is not totally altered are known in the art (H. Neurath, R. L. Hill, The Proteins, Academic Press, New York, 1979). The most commonly occurring exchanges are exchanges between amino acid residues Ala/Ser, Val/Ile, Asp/Glu, Thr/Ser, Ala/Gly, Ala-Thr, Ser/Asn, Ala/Val, Ser/Gly, Thy/Phe, Ala/Pro, Lys/Arg, Asp/Asn, Leu/Ile, Leu/Val, Ala/Glu, Asp/Gly.

Functional molecules or elements may be additionally coupled to the single-domain antibody according to the present disclosure. The functional molecule may be one or more selected from the group consisting of inorganic particles, chemicals, peptides, polypeptides, nucleic acids, carbohydrates, radioactive isotopes and lipids.

The inorganic particles are fluorescent labels or dyes, and may be selected from the group consisting of GFP (Green Fluorescent Protein), YFP (Yellow Fluorescent Protein), BFP (Blue fluorescent protein), CFP (Cyan fluorescent protein), Acridine dyes, Cyanine dyes, fluorone dyes, oxazine dyes, phenanthridine dyes, and rhodamine dyes, but is not limited thereto.

The radioactive isotopes may be at least one selected from the group consisting of $^{18}F$ (fluorine), $^{11}C$ (carbon), $^{15}O$ (oxygen), $^{13}N$ (nitrogen), $^{89}Zr$ (zirconium), $C^{15}O$, $^{13}N$ (ammonia), $H_2^{15}O$, and $^{18}FDG$ (F-Deoxy Glucose), but is not limited thereto.

The chemical substance may be a substance that inhibits diseases related to angiogenesis. The chemical substance that inhibits angiogenesis related diseases may be combined with the single-domain antibody according to the present disclosure without limitation. For example, the chemical substance may be an angiogenesis inhibitor, an anticancer agent, or an atherosclerosis inhibitor.

The angiogenesis inhibitor, may be, for example, avastin, itraconazole, carboxyamidotriazole, suramin, SU5416, thrombospondin, sorafenib, sunitinib, pazopanib, everolimus, and mixtures thereof, but is not limited thereto.

The anticancer agent may be, for example, acivicin, aclarubicin, acodazole, acronycin, adozelesin, alanosine, aldesleukin, allopurinol sodium, altretamine, aminoglutethimide, amonafide, ampligen, amsacrine, androgens, anguidine, apidicholine glycinate, asarey, asparaginase, 5-azacytidine, azathioprine, *Bacillus* calmette-guerin (BCG), Bakers antipol, beta-2-dioxythioguanosine, bisantrene HCl, Bleomycin Sulfate, Bulseophan, Butionine Sulfoximine, BWA 773U82, BW 502U83/HCl, BW 7U85 Mesylate, cerasemide, carbetimer, carboplatin, carmustine, chlorambucil, chloroquinoxaline-sulfonamide, chlorozotocin, chromomycin A3, cisplatin, cladribine, corticosteroids, corynebacterium parboom, CPT-11, crisnatole, cyclocytidine, cyclophosphamide, cytarabine, cytembena, davis maleate, decarbazine, dactinomycin, daunorubicin HCl, deazauridine, dexrazoic acid, dianhydro galactitol, diaziquone, dibromodulcitol, didemin B, diethyldithiocarbamate, diclicoaldehyde, dihydro-5-azacytine, doxorubicin, ethinomycin, dedatrexate, edelfosine, eflonitin, elliots solution, elsamitrusin, epirubicin, esorubicin, estramustine phosphate, estrogen, ethanidazole, ethiophos, etoposide, padrazole, pajarabine, fenretinide, filgrastim, finasteride, flavone acetic acid, phloxuridine, fludarabine phosphate, 5'-fluorouracil, Fluosol, flutamide, gallium nitrate, gemcitabine, goserelin acetate, hepsulpam, hexamethylene bisacetamide, homoharingtonine, hydrazine sulfate, 4-hydroxyandrostenedione, hydrodiurea, Idarubicin HCl, ifosfamide, 4-ipomeanol, iproplatin, isotretinoin, leucovorin calcium, leuprolide acetate, levamisol, liposome daunorubicin, liposome capture doxorubicin, lomustine, lonidamine, mytansine, mechloretamine hydrochloride, melphalan, menogaryl, merbaron, 6-mercaptopurine, mesna, methanol extract of *Bacillus* calete-guerine, methotrexate, N-methylformamide, mifepristone, mitoguazone, mitomycin-C, mitotan, mitoxantrone hydrochloride, monocyte/macrophage colony-stimulating factor, nabilone, napoxidine, neocarzinostatin, octreotide acetate, ormaplatin, oxaliplatin, paclitaxel, palla, pentostatin, piperazindione, pipobroman, pirarubicin, pyritrexim, pyroxantrone hydrochloride, PIXY-321, plicamycin, porfimer sodium, prednimustine, procarbazine, progestins, pyrazofurin, rajok acid, sargramostim, semustine, spirogermanium, spiromustine, streptonigrin, streptozosine, sulophener, suramin sodium, tamoxifen, taxorere, tegafur, teniposide, terephthalamidine, teroxirone, thioguanine, thiotepa, thymidine injection, thiazofurine, topotecan, toremifene, tretinoin, trifluoperazine hydrochloride, trifluridine, trimetrexate, TNF (tumor necrosis factor), uracil mustard, vinblastine sulfate, vincristine sulfate, vindesine, vinorelbine, vinzolidine, Yoshi 864, zorubicin, cytosine arabinoside, etoposide, melphalan, taxol, and mixtures thereof, but are not limited thereto.

The peptide or polypeptide as a functional molecule is not particularly limited, and may include hormones, hormone analogs, enzymes, enzyme inhibitors, signaling proteins or portions thereof, antibodies or portions thereof, single chain antibodies, binding proteins or binding domains thereof, antigens, adhesion proteins, structural proteins, regulatory proteins, toxin proteins, cytokines, transcriptional regulatory factors, blood coagulation factors, and vaccines, but is not limited thereto. More specifically, the peptide or polypeptide additionally bound to the single-domain antibody according to the present disclosure may include insulin, IGF-1 (insulin-like growth factor 1), growth hormone, erythropoietin, G-CSFs (granulocyte-colony stimulating factors), GM-CSFs (granulocyte/macrophage-colony stimulating factors), interferon alpha, interferon beta, interferon gamma, interleukin-1 alpha and beta, interleukin-3, interleukin-4, interleukin-6, interleukin-2, EGFs (epidermal growth factors), calcitonin, ACTH (adrenocorticotropic hormone), TNF (tumor necrosis factor), atobisban, buserelin, cetrorelix, deslorelin, desmopressin, dynorphin A (1-13), elcatonin, eleidosin, eptifibatide, GHRHII (growth hormone releasing hormone-II), gonadorelin, goserelin, histrelin, leuprorelin, lypressin, octreotide, oxytocin, pitressin, secretin, sincalide, terlipressin, thymopentin, thymosine α1, triptorelin, bivalirudin, carbetocin, cyclosporine, exedine, lanreotide, LHRH (luteinizing hormone-releasing hormone), nafarelin, parathyroid hormone, pramlintide, T-20 (enfuvirtide), thymalfasin, ziconotide, lysine, lysine A chain, pseudomonas exotoxin, diphtheria toxin, pokeweed antiviral protein, abrin, abrin A chain, cobra venom factor, gelonin, saporin, modeccin, volkensin, viscumin, *Clostridium perfringens* phospholipase C and bovine pancreatic ribonuclease, but may not be limited thereto.

In one example, a sequence of a suitable peptide linker used when the functional molecule bound to the single-domain antibody is a peptide or a polypeptide may be selected in consideration of the following factors: (a) ability at which the liner is applied to a flexible elongated structure; (b) the ability not to create secondary structures that interact with the epitope; and (c) the absence of a hydrophobic moiety capable of reacting with the epitope or a moiety having a charge. The preferred peptide linker may include Gly, Asn and Ser moieties. Other neutral amino acids such as Thr and Ala may also be included in the linker sequence.

Further, the present disclosure provides a recombinant vector containing at least one selected from the group consisting of base sequences represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In the present disclosure, the term "vector" refers means for expressing a target gene in a host cell, and may include a plasmid vector, a phagemid vector; a cozmid vector; viral vectors such as bacteriophage vector, adenovirus vector, retrovirus vector, and adeno-associated virus vector. Preferably, the vector is a phagemid vector or a plasmid vector.

The recombinant vector may be represented as the vector map of FIG. 10A or FIG. 10B. Specifically, FIG. 10A shows the expression vector map (pALT-Avb3 VHH25) of the single-domain antibody VHH-25 containing the His6 tag. FIG. 10B shows the expression vector map (pALT-Avb3 VHH25K1) of the single-domain antibody VHH-25 containing the Lysin and His6 tags. As long as the vector achieves the purpose for expressing the single-domain antibody according to the present disclosure, the vector is not limited thereto.

According to a preferred embodiment according to the present disclosure, a nucleic acid molecule encoding a single-domain antibody in a vector according to the present disclosure is operatively linked with a promoter.

In the present disclosure, the term "operably linked" refers to a functional linkage between a nucleic acid expression regulatory sequence (e.g., a promoter, a signal sequence, or an array of transcriptional control factor binding sites) and another nucleic acid sequence. Thus, the regulatory sequence controls the transcription and/or translation of the other nucleic acid sequence.

The vector system according to the present disclosure may be constructed through various methods known in the art. A specific example of the method is disclosed in Sambrook et al. (2001), Molecular Cloning, A Laboratory Manual, Cold Spring Harbor Laboratory Press, which is incorporated herein by reference.

The vector according to the present disclosure may typically be constructed as vectors for cloning or as vectors for expression. Further, the vector according to the present disclosure may be constructed using prokaryotic or eukaryotic cells as a host. When the vector according to the present disclosure is an expression vector and a prokaryotic cell is a host, strong promoter capable of proceeding transcription (e.g., tac promoter, lac promoter, lacUV5 promoter, lpp promoter, pLλ promoter, pRλ promoter, rac5 promoter, amp promoter, recA promoter, SP6 promoter, trp promoter, and T7 promoter, etc.), a ribosome binding site for initiation of translation and a transcription/translation termination sequence may be contained in the vector. When $E.$ $coli$ (e.g., HB101, BL21, DH5α, etc.) is used as a host cell, the promoter and operator sites of the $E.$ $coli$ tryptophan biosynthetic pathway (Yanofsky, C. (1984), J. Bacteriol., 158: 1018-1024) and the left-handed promoter of phage λ (pLλ promoter, Herskowitz, I. and Hagen, D. (1980), Ann. Rev. Genet., 14:399-445) may be used as a regulatory site.

In one example, a vector that may be used in the present disclosure may be produced by manipulating a plasmid often used in the art (e.g. pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19, etc.), phagemid (e.g., pComb3X), phage (e.g., λgt4·B, λ-Charon and M13, etc.) or virus (e.g., SV40, etc.).

In one example, when the vector according to the present disclosure is an expression vector and a eukaryotic cell is a host, the promoters derived from the genome of mammalian cells (e.g. metallotionine promoter) or promoters derived from mammalian viruses (e.g. adenovirus late promoter, vaccinia virus 7.5K promoter, SV40 promoter, cytomegalovirus promoter and HSV pseudo-promoter) may be used. The vector generally has a polyadenylation sequence as a transcription termination sequence.

The vector according to the present disclosure may be fused with other sequences as necessary to facilitate purification of the protein. Sequences to be fused therewith may include, for example, glutathione S-transferase (Pharmacia, USA), maltose binding protein (NEB, USA), FLAG (IBI, USA) and 6× His (hexahistidine; Quiagen, USA) and the like, but are not limited thereto. Further, the expression vector according to the present disclosure may contain an antibiotic resistance gene commonly used in the art as a selection label. Examples of the antibiotic resistance gene include resistance genes to ampicillin, gentamicin, carbenicillin, chloramphenicol, streptomycin, kanamycin, geneticin, neomycin, and tetracycline.

Further, the present disclosure provides a recombinant microorganism transformed with the recombinant vector.

Any host cell known in the art may be used as a host cell capable of stably and continuously cloning and expressing the vector according to the present disclosure. For example, the host cell may include strains of the genus $Bacillus$ such as $Escherichia$ $coli.$ $Bacillus$ $subtilis$ and $Bacillus$ $thuringiensis$, or a prokaryotic host cell such as $Streptomyces,$ $Pseudomonas$ (e.g. $Pseudomonas$ $putida$), $Proteus$ $mirabilis,$ $Staphylococcus$ (e.g., $Staphylocus$ $carnosus$), but is not limited thereto. The host cell is preferably $E.$ $coli$, more preferably $E.$ $coli$ ER2537, $E.$ $coli$ ER2738, $E.$ $coli$ XL-1 Blue, $E.$ $coli$ BL21 (DE3), $E.$ $coli$ JM109, $E.$ $coli$ DH Series, $E.$ $coli$ TOP10. $E.$ $coli$ TG1 and $E.$ $coli$ HB101. In the present disclosure, the single-domain antibody may be overexpressed using $E.$ $coli$ and thus mass production thereof may be realized at low cost.

A method of transporting the vector according to the present disclosure into the host cell may include the CaCl2 method (Cohen, S N et al. (1973), Proc. Nati. Acac. Sci. USA, 9:2110-2114), Hanahan method (Cohen, S N et al. (1973), Proc. Natl. Acac. Sci. USA, 9:2110-2114; and Hanahan, D. (1983). J. Mol. Biol., 166:557-580) and electroporation method (Dower, W. J. et al. (1988), Nucleic. Acids Res., 16:6127-6145).

The vector injected into the host cell may be expressed in the host cell. In this case, a large amount of single-domain antibodies according to the present disclosure may be obtained.

Further, the present disclosure provides a composition for detecting angiogenesis, the composition includes the single-domain antibody.

In the present disclosure, the term "detection" may mean detecting an antigen-antibody complex and may be performed using various labels. Specific examples of the label include enzymes, fluorescent substances, ligands, luminescent substances, microparticles, or radioactive isotope. Enzymes used as detection labels include acetylcholinesterase, alkaline phosphatase, β-D-galactosidase, horseradish peroxidase and β-latamase, and the like. The fluorescent material includes fluorescein, $Eu^{3+}$, $Eu^{3+}$ chelate or cryptate, etc. The ligand includes a biotin derivative, etc. The luminescent material includes acridinium ester and isoluminol derivative. The microparticles includes colloidal gold and colored latex. The radioactive isotope includes $^{57}Co$, $^{3}H$, $^{125}I$ and $^{125}I$-Bonton Hunter reagent.

Further, the present disclosure provides a kit for detecting angiogenesis, the kit includes the single-domain antibody.

The kit according to the present disclosure may contain not only a single-domain antibody according to the present disclosure, but also a color development substrate solution to react with the label, a washing solution to be used in each reaction step, and an enzyme reaction stop solution. However, the disclosure is not limited thereto.

Further, the present disclosure provides a composition for diagnosing angiogenesis-related diseases, the composition includes the single-domain antibody.

In one embodiment of the present disclosure, the angiogenesis-related disease may include at least one selected from the group consisting of arteriosclerosis, cancer, diabetic retinopathy, angiogenesis glaucoma, posterior lens fibrosis, proliferative vitreous retinopathy, immature retinopathy, ophthalmic inflammation, corneal ulcer, conical cornea, macular degeneration, Sjogren's syndrome, myopia eye tumor, corneal graft rejection, abnormal wound union, trachoma, bone disease, rheumatoid arthritis, osteoarthritis, septicemia arthritis, hemangiomas, angiofibroma, psoriasis, pyogenic granuloma, proteinuria, abdominal aortic aneurysm disease, degenerative cartilage loss due to traumatic joint damage, neuro demyelination disease, liver cirrhosis, glomerular disease, immature rupture of the embryonic membrane, inflammatory bowel disease, periodontal ligament disease, restenosis, inflammation of the central nervous system, Alzheimer's disease, skin aging, thyroid hyperplasia, and Grave's disease. The angiogenesis-related disease is preferably, but not limited to, atherosclerosis or cancer.

In the present disclosure, the cancer may include bile duct cancer, bladder cancer, brain tumor, breast cancer, cervical cancer, chorionic cancer, colon cancer, endometrial cancer, esophageal cancer, gastric cancer, multiple myeloma. AIDS-related leukemia and adult T-cell lymphoma/leukemia, intraepithelial cancer, liver cancer, lung cancer, lymphoma, neuroblastoma, oral cancer, ovarian cancer, pancreatic cancer, prostate cancer, rectal cancer, sarcoma, skin cancer, testicular cancer, thyroid cancer or renal cell carcinoma, and cancers in which $\alpha_v\beta_3$ integrin are expressed. However, the disclosure is not limited thereto.

Further, the present disclosure provides a preparation method of an $\alpha_v\beta_3$ integrin targeting single-domain antibody, the method including: (1) culturing a recombinant microorganism transformed with a recombinant vector containing at least one selected from the group consisting of base sequences represented by SEQ ID NO: 1, SEQ ID NO: 2, SEQ ID NO: 3, SEQ ID NO: 4, SEQ ID NO: 5, SEQ ID NO: 6, SEQ ID NO: 7 SEQ ID NO: 8, SEQ ID NO: 9 and SEQ ID NO: 10, and (2) expressing a single-domain antibody for $\alpha_v\beta_3$ integrin in the microorganism.

In the present disclosure, the term "cultivation" means growing microorganisms under appropriately artificially controlled environmental conditions.

The microorganism may be grown in a conventional medium. The medium contains nutrients required by a culture target, that is, a microorganism in order to cultivate a specific microorganism, and may additionally contain a material for a special purpose. The medium may be referred to as an incubator or culture liquid and contains natural, synthetic, or selective medium.

The medium used for cultivation must meet the requirements for a specific strain in an appropriate manner by controlling a temperature, pH, etc. in a conventional medium containing an appropriate carbon source, nitrogen source, amino acid, vitamin, etc. The carbon source may include a mixed sugar of glucose and xylose as the main carbon source. In addition, the carbon source may further include sugars and carbohydrates such as sucrose, lactose, fructose, maltose, starch, cellulose, oils and fats such as soybean oil, sunflower oil, castor oil, and coconut oil, fatty acids such as palmitic acid, stearic acid and linoleic acid, alcohols such as glycerol and ethanol, and organic acids such as acetic acid. These materials may be used individually or as a mixture thereof. The nitrogen source that may be used may include ammonia, ammonium sulfate, inorganic nitrogen sources such as ammonium chloride, ammonium acetate, ammonium phosphate, ammonium carbonate, and ammonium nitrate; organic nitrogen sources such as amino acids such as glutamic acid, methionine, glutamine, and peptone, NZ-amine, meat extract, yeast extract, malt extract, corn steep liquor, casein hydrolysate, fish or a decomposition product thereof, skim soybean cake or a decomposition product thereof. These nitrogen sources may be used alone or in combination thereof. The medium may contain first potassium phosphate, second potassium phosphate and a corresponding sodium-containing salt as a phosphate source. The phosphate source that may be used may include potassium dihydrogen phosphate or dipotassium hydrogen phosphate or the corresponding sodium-containing salt. Further, the inorganic compound may include sodium chloride, calcium chloride, iron chloride, magnesium sulfate, iron sulfate, manganese sulfate and calcium carbonate. Finally, in addition to the materials, essential growth materials such as amino acids and vitamins may be used.

Further, precursors suitable for the culture medium may be used. The raw materials as described above may be added in a batch, fed-batch or continuous manner to the culture during the culture process, but are not particularly limited thereto. Basic compounds such as sodium hydroxide, potassium hydroxide, ammonia, or acid compounds such as phosphoric acid or sulfuric acid may be used in an appropriate manner to adjust the pH of the culture.

Further, the present disclosure provides a method for screening an angiogenesis inhibitor or promoter, the method comprising (1) treating a biological sample isolated from a specimen or an animal model with candidate drugs to be analyzed; (2) binding the $\alpha_v\beta_3$ integrin targeting single-domain antibody to the sample and measuring a level of $\alpha_v\beta_3$ integrin protein; and (3) selecting a candidate drug by which the protein level of the (2) is suppressed or enhanced compared to a control.

Further, the present disclosure provides a method for providing information for diagnosis of angiogenesis-related diseases, the method including (a) binding the $\alpha_v\beta_3$ integrin targeting single-domain antibody to a biological sample isolated from a specimen and measuring a level of $\alpha_v\beta_3$ integrin protein; and (b) comparing the level of the $\alpha_v\beta_3$ integrin protein with a reference value obtained from a control sample.

The single-domain antibody according to the present disclosure may be provided as a pharmaceutical composition for the prevention and treatment of angiogenesis-related diseases when combined with a functional molecule.

The pharmaceutical composition according to the present disclosure may additionally contain an adjuvant in addition to the single-domain antibody. The adjuvant may be used without limitation, as long as it is known in the art. However, for example, the pharmaceutical composition may further contain a Freund's complete adjuvant or incomplete adjuvant, thereby increasing the effect.

The pharmaceutical composition according to the present disclosure may be prepared in the form of incorporating an active ingredient into a pharmaceutically acceptable carrier. In this connection, the pharmaceutically acceptable carrier includes carriers, excipients, and diluents commonly used in the pharmaceutical field. The pharmaceutically acceptable carriers that may be used for pharmaceutical composition according to the present disclosure may include lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinyl pyrrolidone, water, methylhydroxybenzoate, propylhydroxybenzoate, talc, magnesium stearate, and mineral oils. However, the present disclosure is limited thereto.

The pharmaceutical composition according to the present disclosure may be formulated and used in the form of oral dosage forms such as powders, granules, tablets, capsules, suspensions, emulsions, syrups, and aerosols, external preparations, suppositories or sterile injectable solutions according to conventional methods.

The formulation may be prepared using diluents or excipients such as commonly used fillers, extenders, binders, wetting agents, disintegrants, and surfactants. Solid preparations for oral administration include tablets, pills, powders, granules, capsules, etc. The solid preparation may be prepared by mixing at least one excipient such as starch, calcium carbonate, sucrose, lactose, and gelatin, with the active ingredient. Further, in addition to simple excipients, lubricants such as magnesium stearate and talc may be used. Liquid preparations for oral administration include suspensions, solvents, emulsions, syrups, etc. Various excipients, such as wetting agents, sweeteners, fragrances, and preservatives, are included therein in addition to water and liquid paraffin, which are commonly used diluents. Preparations for parenteral administration include sterile aqueous solutions, non-aqueous solutions, suspensions, emulsions, lyophilized preparations, and suppositories. The non-aqueous solvent and suspension may include propylene glycol, polyethylene glycol, vegetable oil such as olive oil, injectable ester such as ethyloleate. A base for suppositories may include witepsol, tween 61, cacao butter, laurin paper, glycerogelatin, and the like.

The pharmaceutical composition according to the present disclosure may be administered to an individual by various routes. All modes of administration may be considered, for example, including oral, intravenous, intramuscular, subcutaneous, intraperitoneal injection.

The dosage of the pharmaceutical composition according to the present disclosure is selected in consideration of the individual's age, weight, sex, and physical condition. It is obvious that the concentration of the single-domain antibody contained in the pharmaceutical composition may be selected in various ways depending on the subject. Preferably, the single-domain antibody is contained in a concentration of 0.01 μg/ml to 5,000 μg/ml in the pharmaceutical composition. When the concentration is lower than 0.01 μg/ml, pharmaceutical activity may not occur. When the concentration exceeds 5,000 μg/ml, the single-domain antibody may be toxic to the human body.

EXAMPLES

The present disclosure will be described in more detail through the following Examples. However, the following Example is only intended for specifying the content according to the present disclosure, and the present disclosure is not limited thereto.

<Example 1> Immune Response Induction and Serum Quantification in Camels

<1-1> Induction of Immune Response in Camels

In order to induce an immune response after inoculating camels with a recombinant $\alpha_v\beta_3$ integrin protein having cross-activity in humans or mice, the following experiment was performed.

Specifically, 2 mg/ml human $\alpha_v\beta_3$ integrin ITGAVB3 was used as an antigen, mixed in advance with 1 mg/ml PBS, and the mixture was divided into 800 μl per EP tube at 4° C. First, as an adjuvant, Complete Freund's Adjuvant (CFA) (Sigma) was used, and then incomplete Freund's Adjuvant (IFA) (Sigma) was used. The antigen and adjuvant were thoroughly mixed to prepare a stable emulsion. The emulsion was administered subcutaneously to a portion around the back of a camel (*Camelus bacterianus*). Thereafter, the first immunization was induced by mixing 2 ml of the collected blood (collected from 1 ml of pre-immune serum) with complete Freud adjuvant (CFA) and 600 μg antigen mixture/camel. Boost immunity was induced by mixing the blood with incomplete Freud adjuvant (IFA) and 600 μg antigen mixture/camel. A total of 4 times were performed at intervals of 2 weeks, and 50 ml of blood was collected 15 days after the fourth boost immunization was performed.

<1-2> Serum Titer of Immunity Induced Camels

ELISA was performed as follows to identify the titer of the immune-induced camel serum of Example 1-1.

The serum titer was measured the day after the fourth boost immunization was performed. 100 μL of targeting protein was coated with coating buffer containing 10 μL antigen and was incubated overnight at 4° C. After washing twice with a washing buffer (PBST, PBS containing 0.05% Tween-20), the well was blocked using 350 μL blocking buffer (PBSM, PBS containing 4% milk) and was placed at room temperature for 2 hours. Thereafter, the blocking buffer was removed. The plate was placed on a clean side of a paper towel while being washed for 5 times using the washing buffer. 100 μL diluted serum was added thereto, incubated at room temperature for 1 hour, and washed 5 times with washing buffer. Rabbit anti-camel IgG pAb-HRP was diluted with PBS, and 100 μL diluted antibody was added to each well, followed by incubation at room temperature for 1 hour. A HRP (horseradish peroxidase) substrate solution was prepared as follows: A stock solution of OPD (o-phenylenediamine) was prepared by dissolving 22 mg OPD (Sigma) in 100 mL of 50 mM sodium citrate at pH 4.0. After the filter was sterilized and stored at 4 degrees C., 36 μL 30% $H_2O_2$ was added to 21 mL OPD stock solution before the detection step. 100 μL substrate solution was added to each well and incubated for 30 minutes at room temperature. Each plate was analyzed using a microplate reader set at 490 nm. The results are shown in Table 1 below.

As shown in Table 1, it was identified that the serum of the immune-induced camel of Example 1-1 exhibited a titer of 1/12,800. Accordingly, the last boost immunization was performed the next day after the serum titer was measured, and peripheral blood leukocytes (PBLs) were obtained on the next day, and were used for RNA extraction and cDNA analysis.

TABLE 1

| Dilution | Coating:A5B3 |
|---|---|
| 1/400 | 1.399 |
| 1/800 | 1.052 |
| 1/1600 | 0.714 |
| 1/3200 | 0.416 |
| 1/6400 | 0.262 |
| 1/12800* | 0.156* |
| 1/25600 | 0.1 |
| 1/51200 | 0.126 |
| PBS | 0.078 |

*the end titer
a. Coating: A5B3, 0.5 ug/well
b. 1st Ab: antisera
c. 2nd Ab: HRP-rabbit anti-camel IgG <Example 2> Gene Amplification of Single-Domain Antibody and Gene Library Creation <2-1> RNA Isolation and cDNA Synthesis of Isolated Peripheral Blood Leukocytes (PBLs)

For gene amplification of single-domain antibody according to the present disclosure, RNA isolation and cDNA synthesis of isolated peripheral blood leukocytes (PBLs) were performed as follows.

Specifically, peripheral blood leukocytes (PBLs) were isolated from blood of camel in which the immunity was induced in the Example 1-1 via density gradient centrifugation using the Ficoll Hypaque technique. Total RNA was isolated according to the manufacturer's protocol using the Trizol method. The separated RNA pellet was dried and dissolved in 100 μl DEPC-treated water, and then used for RT-PCR.

An RNase-free 0.5 ml reaction mixture containing 2 μl dNTP mix (Pharmacia, 25 mM each dNTP), 2 μl Oligo-dT primer (200 pMol), 5 μl Super RT buffer, and 26.5 μl DEPC-treated water was prepared. Thereafter, the isolated 10 μl RNA (containing up to 1.5 μg of mRNA) was added to the tube, mixed, and pipetted. A drop of mineral oil (Sigma) was added to the mixture which in turn was heated at 67 degrees C. for 5 minutes in a thermocycler (Biometra, Trio Thermoblock) to destroy the secondary structure. Then, after cooling to 42 degrees C., 2 μl RNAsin (Promega) and 2.5 μl Super RT (HT Biotechnology Ltd, Cambridge, UK) were added thereto and incubation thereof occurred for 1 hour at 42 degrees C. The mixture was heated at 100° C. for 3 minutes (punctured with a sterilized needle). Thereafter, the product containing the single-stranded cDNA was centrifuged and stored at −20 degrees C.

<2-2> Amplification of Single-Domain Antibody Expression Cassette According to the Present Disclosure The cDNA synthesized in the 2-1 was quantified by UV spectroscopy. For amplification of VH-CH1-FC/VHH-FC gene, FC downstream primer. VH/VHH-FR1 upstream primer and cDNA synthesized in the 2-1 as diluted 200 times were used as templates to perform the first PCR amplification of the VH-CH1-FC/VHH-FC gene. The first PCR amplified DNA band of about 600 bp was collected, and a Gel purification process was performed using Qiagen Kit. Thereafter, in order to amplify the VHH gene, the second PCR amplification was performed using the VHH-FR4 downstream primer, the VHH-FR1 upstream primer, and the purified DNA. The results are shown in FIG. 1 and FIG. 2.

As shown in FIG. 1, based on a result of performing the first PCR amplification, it was identified that bands of about 600 bp and 900 bp appeared.

Further, as shown in FIG. 2, based on a result of performing the second PCR amplification, the DNA band of the single-domain antibody according to the present disclosure as amplified at about 600 bp could be identified.

<Example 3> Production of Single-Domain Antibody Library According to the Present Disclosure The selection and search of an antibody that recognizes $α_vβ_3$ integrin from the single-domain antibody gene library as prepared in Example 2 was performed using a phage display method. Thus, a single-domain antibody clone library was prepared.

<3-1> Insertion and Transformation of Single-Domain Antibody Gene According to the Present Disclosure into Phagemid After cutting the single-domain antibody gene according to the present disclosure and phagemid, the cut gene was inserted into the phagemid. A following process was carried out to transform the same in E. coli TG1. The second PCR product obtained in the 2-2 and pDisplay-3M™ were cleaved with BssHII and NheI, and purified simultaneously with Qiagen kit. Thereafter, the DNA fragment was ligated using NEB's T4 DNA ligase, and then the product was transformed via electro-transformation into E. coli TG1 cells. The results are shown in FIG. 3 and FIG. 4.

As shown in FIG. 3 and FIG. 4, based on the results of identifying the gel-electrophoresis of the single domain gene cut for insertion into phagemid and the phagemid cut to clone the single-domain antibody gene, it was identified that each of the bands corresponding thereto appeared clearly.

<3-2> Phage Packaging and Library Preparation

The E. coli TG1 transformed in the 3-1 was infected with the M13K07 helper phage. In order to increase the phage that specifically binds to the antigen, a process was performed as follows.

In order to prepare the M13K07 helper phage, log-phase TG1 cells and M13K07 phage were infected with different dilutions for 30 minutes at 37° C. and inoculated on agar of 2TY plates. After inoculating and culturing a small plaque in the 3 mL liquid 2TY medium, 30 μL of overnight cultured TG1 cells were added thereto and then culturing occurred at 37 degrees C. for 2 hours. After diluting the culture medium of 1 L 2TY medium and incubating for 1 hour, 50 μg/mL kanamycin was added thereto and culturing occurred under the condition of 37 degrees C. for 16 hours. Cells were removed by centrifugation (10 minutes, 5,000 g), and 0.25 volume of phage precipitate was added thereto to precipitate phage from the supernatant. After incubation on ice for 30 minutes, centrifugation (10 minutes, 5,000 g) was performed to obtain phage particles. After resuspending the pellet with 5 mL PBS, the pellet passed through a 0.22-μm filter. Helper phages were identified by counting the number of plaque-forming units (pfu) on a 2TY plate for the top-agar layer containing 100 μL TG1 (saturated culture). After diluting the phage stock solution to $1×10^{13}$ pfu/mL, the phage stock solution was stored at −20 degrees C.

Further, in order to prepare the library phage, the library glycerol stock and 500 mL 2TY-G were incubated and incubated at 37 degrees C. with shaking at 250 rpm until the optical concentration reached 0.8 to 0.9 at 600 nm. M13KO7 helper phage was added thereto so that the final concentration was $5×10^9$ pfu/mL, and incubated at 37° C. for 30 minutes without shaking, followed by appropriate shaking (200 rpm) to perform phage infection for 30 minutes. Thereafter, the cells were collected by centrifugation at 2200 g for 15 minutes, and the pellet was resuspended in the same amount of 2TY-AK. Rapid shaking (300 rpm) was performed and incubation occurred overnight at 30 degrees C. Cells were pelleted by centrifugation at 4 degrees C., 15 minutes, and 7,000 g, and a supernatant containing phage was obtained into a pre-cooled 1 L bottle. Thereafter, 0.3 volume of the phage precipitant was added thereto and mixed with each other, and the phage was precipitated on ice for 1 hour. Then, the phage was pelletized by centrifugation twice under conditions of 4 degrees C., 15 minutes, and 7,000 g. The supernatant was removed and the pellet was resuspended in 8 mL PBS. Thereafter, the phage was centrifuged at 12,000 g for 10 minutes, and the phage was collected through the supernatant. Finally, the phage stock dilution was infected with TG1 cells, plated on 2TY-AG, and cultured, and then the number of ampicillin-resistant colonies that appeared was identified. Via the process, we built a single domain library according to the present disclosure. Its titer was measured. The results are shown in Table 2.

As shown in Table 2, it was identified that the single-domain antibody library according to the present disclosure had a titer of $5.16 \times 10^{13}$ pfu/mL.

TABLE 2

| Items | Diversity | Positive percentage % | Titers (pfu/ml) |
|---|---|---|---|
| A5b3 VHH library | $2.33 \times 10^8$ | 8/10 | $5.16 \times 10^{13}$ |

<3-3> Identification of Gene Insertion in Single-Domain Antibody Library According to the Present Disclosure, and DNA Alignment 10 representative clones were selected from the single domain library according to the present disclosure selected in the 3-2, and QC colony PCR thereon was performed. The results are shown in FIG. 5.

As shown in FIG. 5, 9 of the 10 clones were identified to have about 600 bp, and thus the single domain according to the present disclosure was correctly inserted thereto.

Via the same process as the above process, DNA sequencing was performed on 20 clones in the library in which a single domain according to the present disclosure was correctly inserted. S6 downstream primer was used and DNA was aligned. The results are shown in FIG. 6A and FIG. 6I.

Figures 6H, 6I:
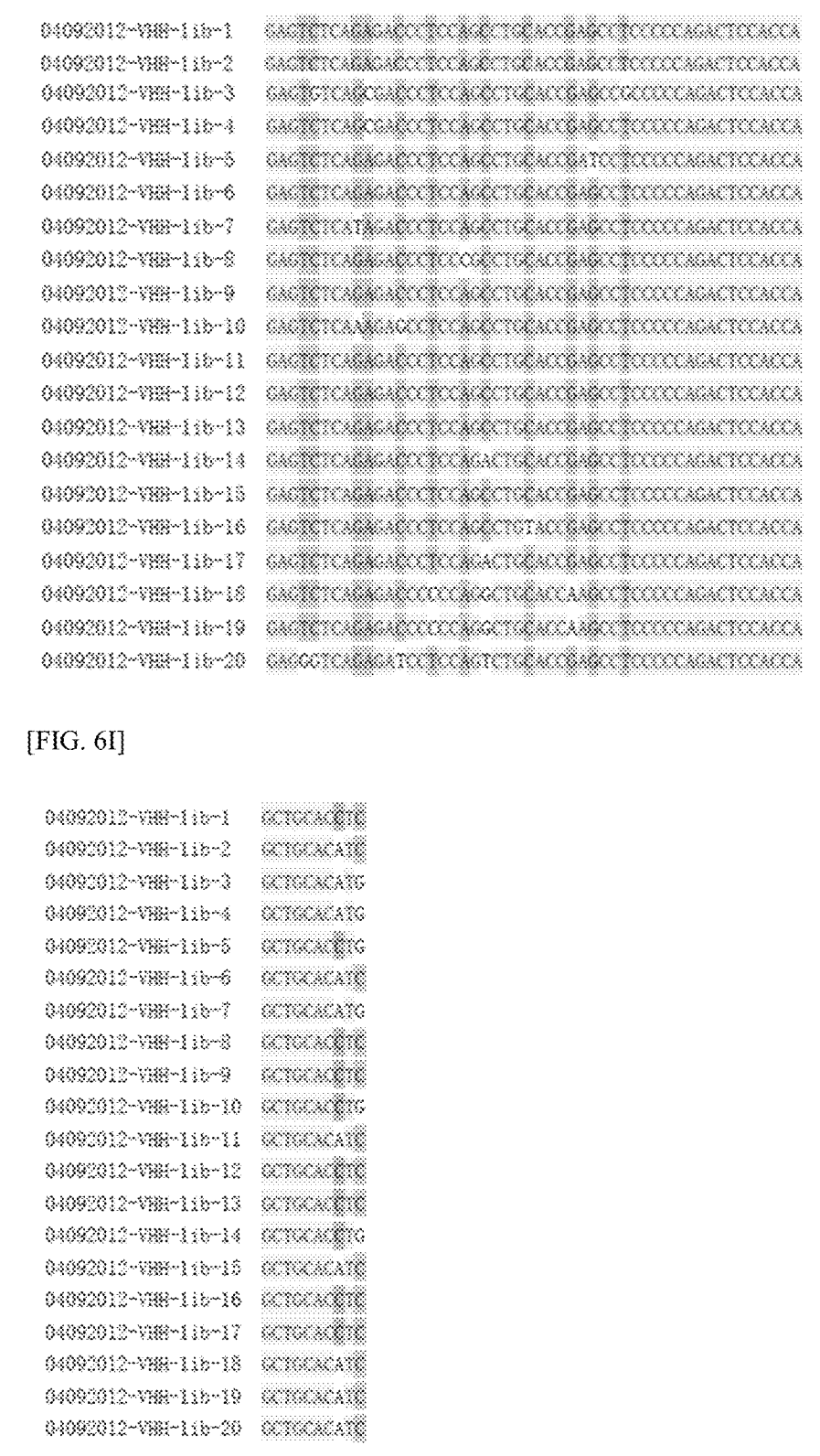

As shown in FIG. 6A and FIG. 6I, 20 clones were identified to exhibit diversity.

<Example 4> Specific Antibody Selection Via Panning

In order to perform panning in the single-domain antibody clone library according to the present disclosure constructed in the Example 3, 5 µg/mL to 30 µg/mL of a target was coated and incubated for 2 hours at 4° C. Thereafter, the wells were washed three times with a washing buffer, and then the blocking buffer was filled, incubation occurred overnight at 4 degrees C., and washing was performed once with the washing buffer. PBS-M (2% milk) was added to pre-blocked wells (non-coated) to mix the original library phage and incubation occurred at room temperature for 30 minutes. Thereafter, phages are placed in the pre-blocked (coated) wells and incubation occurred for 1 hour at room temperature. Washing was performed 10 times with washing buffer, and the bound phage was eluted via trypsin digestion. The eluate was titrated and amplified. The results are shown in FIG. 7 and Table 3.

As shown in FIG. 7, $\alpha_v\beta_3$ integrin ITGAVB3 antigen to be used for specific antibody selection via panning was verified using SDS-PAGE.

Further, as shown in Table 3, phage library candidates having strong binding to the target protein were selected via a three-step selection process.

TABLE 3

| Round | Conditions | Input | Output | Enriching factor |
|---|---|---|---|---|
| 1st | Target protein: ITGAVB3 30 ug/ml<br>Washing: 0.1% PBS-Tween 20, 9 times<br>Elution: Trypsin digestion<br>Pre counter select: 2% M-PBS | $1.12 \times 10^{11}$ | $1.61 \times 10^5$ | $6.96 \times 10^5$ |
| 2nd-P | Target protein: ITGAVB3 30 ug/ml<br>Washing: 0.2% PBS-Tween 20, 9 times<br>Elution: Trypsin digestion<br>Pre counter select: 2% M-PBS | $9.04 \times 10^{10}$ | $2.93 \times 10^4$ | $3.09 \times 10^6$ |
| 2nd-N | Target protein: no coating<br>Washing: 0.2% PBS-Tween 20, 9 times<br>Elution: Trypsin digestion<br>Pre counter select: 2% M-PBS | $2.26 \times 10^{10}$ | $2.6 \times 10^3$ | $8.69 \times 10^6$ |
| 3rd-P | Target protein: ITGAVB3 30 ug/ml<br>Washing: 0.2% PBS-Tween 20, 9 times<br>Elution: Trypsin digestion<br>Pre counter select: 2% M-PBS | $1.1 \times 10^{11}$ | $2.0 \times 10^6$ | $5.5 \times 10^4$ |
| 3rd-N | Target protein: no coating<br>Washing: 0.2% PBS-Tween 20, 9 times<br>Elution: Trypsin digestion<br>Pre counter select: 2% M-PBS | $2.76 \times 10^{10}$ | $6.4 \times 10^2$ | $4.31 \times 10^7$ |

<Example 5> Analysis of $\alpha_v\beta_3$ Integrin-Specific Single-Domain Antibody Using ELISA After the panning process of Example 4, 40 single-domain antibody phage clones were extracted, and the binding ability thereof to $\alpha_v\beta_3$ integrin-specific single-domain antibody was analyzed using ELISA.

Specifically, in order to prepare a single clone of antibody-displaying phages, an eluate of a single clone was inoculated into 5 mL 2YT-AG medium and culturing thereof occurred overnight at 37° C. A glycerol stock for each clone was prepared and cultured overnight, and 100 µL culture was put in 20 mL of 2YT-AG medium and cultured. The culture was carried out for several hours at 37 degrees C. until the optical density of OD600 reached 0.4 to 0.5. M13KO7 helper phage was added in 20 multiple infections (that is, number of phage particles/host cells). The cells were incubated at 37° C. for 30 minutes, and the cells were infected while shaking for 30 minutes. Infected cells were collected via centrifugation (10 minutes at 5,000 g), resuspended in 2YT-AK, and incubated at 30 degrees C. for 16 hours. Thereafter, phage particles were precipitated in the supernatant, and the phage pellet was resuspended in 1 mL PBS and centrifuged (10 minutes at 5,000 g) to remove cell debris. Ab fragments irrelevant to phage particles were removed, phage pellets were removed in 250 μL PBS, and centrifugation was performed again.

Further, in order to perform phage ELISA, 2.5 μg/mL to 5 sg/mL of a target protein and a control protein were coated at 4 degrees C. using a coating buffer, and the wells were washed 3 times with 200 μL washing buffer per well. The wells were blocked with 200 μL PBS-M for two hours at room temperature. The blocking buffer was removed and the plate was washed 6 times with the washing solution. Thereafter, 100 μL of phage solution was added to the washing buffer per well and incubation was executed at room temperature for 1 to 2 hours. Then, washing was performed 6 times with washing buffer. HRP-binding anti-M13 antibody (GE healthcare) was diluted with 1:5,000 blocking buffer. 100 μL of diluted conjugate was added onto each well, and incubation was performed at room temperature for 1 hour, and washing was carried out 6 times with washing buffer. The HRP substrate solution was prepared as follows: A stock solution of OPD was prepared by dissolving 22 mg OPD (Sigma) in 100 mL of 50 mg sodium citrate (pH 4.0), and 36 μL 30% $H_2O_2$ was added to 21 mL of OPL stock solution immediately before the detection step. 100 μL of substrate solution was added to each well and incubation was performed for 30 minutes at room temperature. Plates were analyzed using a micro plate reader set at 490 nm. Table 4 shows the results of analyzing the clones.

As shown in Table 4, it was identified that all 40 clones strongly bind to $\alpha_v\beta_3$ integrin.

TABLE 4

| Clones | Coating: ITGAVB3 | No coating |
|---|---|---|
| 1 | 1.887 | 0.079 |
| 2 | 2.017 | 0.081 |
| 3 | 1.881 | 0.084 |
| 4 | 2.163 | 0.084 |
| 5 | 1.940 | 0.084 |
| 6 | 1.901 | 0.086 |
| 7 | 1.991 | 0.090 |
| 8 | 1.954 | 0.074 |
| 9 | 2.002 | 0.067 |
| 10 | 2.137 | 0.067 |
| 11 | 2.069 | 0.065 |
| 12 | 2.058 | 0.071 |
| 13 | 2.010 | 0.660 |
| 14 | 1.926 | 0.078 |
| 15 | 1.972 | 0.075 |
| 16 | 2.074 | 0.070 |
| 17 | 1.812 | 0.077 |
| 18 | 1.946 | 0.077 |
| 19 | 1.935 | 0.071 |
| 20 | 1.976 | 0.079 |
| 21 | 1.949 | 0.074 |
| 22 | 2.035 | 0.077 |
| 23 | 2.040 | 0.079 |
| 24 | 1.002 | 0.073 |
| 25 | 2.032 | 0.062 |
| 26 | 2.013 | 0.061 |
| 27 | 1.973 | 0.056 |
| 28 | 1.944 | 0.054 |
| 29 | 2.044 | 0.052 |

TABLE 4-continued

| Clones | Coating: ITGAVB3 | No coating |
|---|---|---|
| 30 | 1.971 | 0.060 |
| 31 | 2.052 | 0.057 |
| 32 | 1.875 | 0.053 |
| 33 | 1.865 | 0.077 |
| 34 | 2.008 | 0.069 |
| 35 | 1.829 | 0.055 |
| 36 | 1.975 | 0.066 |
| 37 | 2.091 | 0.058 |
| 38 | 2.116 | 0.064 |
| 39 | 1.804 | 0.068 |
| 40 | 2.044 | 0.058 |
| 1-A | 0.208 | 0.048 |
| 2-A | 0.451 | 0.052 |
| 3-A | 0.984 | 0.054 |
| M13KO7 | 0.090 | 0.050 |
| 1% M-PBS | 0.048 | 0.057 |

<Example 6> DNA Sequencing and Information Analysis of Single-Domain Antibody Clones According to the Present Disclosure To perform DNA sequencing of single-domain antibody clones according to the present disclosure, we inoculated 2 μL glycerol stock TG1 *E. coli* cells with each positive clone (measured by phage ELISA and/or soluble ELISA) plasmid into 5 mL LB-A medium (LB medium having 100 μg/mL ampicillin added thereto) and cultured the cells overnight at 37° C. Plasmids for each positive clone were isolated from the cells using Plasmid Isolation Kit (Qiagen Miniprep kit), and DNA sequencing was performed using L1 and S6 primers.

Further, in order to analyze the information of each single-domain antibody clone, the returned sequence was transformed using Vector NTI®, Version 10, and the protein sequence was aligned. Thereafter, clones encoding the same protein sequence were grouped and analyzed. The results are shown in Table 5, FIG. 8A to FIG. 8C. The single-domain antibody clone according to the present disclosure is exemplified as VHH for convenience.

As shown in Table 5, based on a result of analyzing 40 clone sequences. 10 candidate VHH DNA sequences were identified.

Further, as shown in FIG. 8A to FIG. 8C, clones 14, 11, 29, 17, 15, 28, 12, 19, 13, 21, 27, 16, 18, 20, 30, 23, 24, 25, 22, 26 showing high responses were selected from the 10 groups and their amino acid sequences were shown.

The base sequence of clones VHH-25, VHH-13, VHH-22, VHH-11, VHH-17, VHH-15, VHH-12, VHH-16, VHH-20, VHH-23 exhibiting strong positives among them were represented by SEQ ID NOs: 1 to 10, respectively. The amino acid sequences of VHH-25, VHH-13, and VHH-22 among them were represented by SEQ ID NOs: 11, 12 and 13, respectively.

TABLE 5

| Items | Clones |
|---|---|
| VHH-1 | 11, 14, 1, 31, 9 |
| VHH-2 | 17, 29, 5, 35, 6 |
| VHH-3 | 15, 2, 3, 4, 39 |
| VHH-4 | 12, 19, 28, 32 |
| VHH-5 | 13, 21, 27 |
| VHH-6 | 16, 187, 8, 34, 36 |
| VHH-7 | 20, 30, 38, 40 |

TABLE 5-continued

| Items | Clones |
|---|---|
| VHH-8 | 23, 24, 37 |
| VHH-9 | 25, 10, 33 |
| VHH-10 | 22, 26 |

The ELISA method of Example 5 was used to select single-domain antibody clones from among clones VHH-11, VHH-17, VHH-15, VHH-12, VHH-13, VHH-16, VHH-20, VHH-23, VHH-25, and VHH-22 exhibiting strong positives. The results are shown in Tables 6 and 7.

As shown in Tables 6 and 7, VHH-12, VHH-13, VHH-16, VHH-22, and VHH-25 among the 10 candidate VHH clones exhibited relatively high binding ability.

TABLE 6

| | OD490 | |
|---|---|---|
| Clones | Inducing at 30° C. | Inducing at 37° C. |
| 11 | 0.148 | 0.119 |
| 12 | 1.836 | 1.226 |
| 13 | 0.161 | 0.187 |
| 15 | 0.146 | 0.121 |
| 16 | 2.018 | 1.023 |
| 17 | 0.118 | 0.125 |
| 20 | 0.108 | 0.111 |
| 22 | 1.213 | 0.386 |
| 23 | 0.141 | 0.113 |
| 25 | 1.048 | 0.193 |
| TG1 | | 0.109 |
| TBS | | 0.120 |

TABLE 7

| Clones | Inducing Temp. | Coating ITGAVB3 | No coating |
|---|---|---|---|
| 11 | 30° C. | 0.334 | 0.125 |
| | 37° C. | 0.640 | 0.122 |
| 12 | 30° C. | 1.866 | 0.273 |
| | 37° C. | 1.929 | 0.168 |
| 13 | 30° C. | 2.003 | 0.110 |
| | 37° C. | 2.000 | 0.116 |
| 15 | 30° C. | 0.179 | 0.133 |
| | 37° C. | 0.132 | 0.130 |
| 16 | 30° C. | 1.750 | 0.400 |
| | 37° C. | 1.683 | 0.207 |
| 17 | 30° C. | 0.243 | 0.120 |
| | 37° C. | 0.191 | 0.118 |
| 20 | 30° C. | 0.129 | 0.125 |
| | 37° C. | 0,144 | 0.130 |
| 22 | 30° C. | 1.977 | 0.178 |
| | 37° C. | 1.980 | 0.148 |
| 23 | 30° C. | 0.179 | 0.135 |
| | 37° C. | 0.160 | 0.138 |
| 25 | 30° C. | 2.007 | 0.157 |
| | 37° C. | 2.029 | 0.123 |
| TG1 lysate | — | 0.120 | 0.131 |
| TBS | — | 0.124 | 0.125 |

<Example 7> SPR (Surface Plasmon Resonance) Analysis of Single-Domain Antibody Clones According to the Present Disclosure VHH-13, VHH-22 and VHH-25 were selected from among single-domain antibodies targeting the $\alpha_v\beta_3$ integrin in the Example 6, and were compared with conventional $\alpha_v\beta_3$ integrin antibodies, and thus SPR analysis was performed.

Specifically, a CMDH chip (Carboxymethyl Dextran Hydrogel Surface Sensor Chip, Reichert Technologies) coated with Dextran was mounted on an SPR equipment (Reichert SR7500DC system) to perform immobilization of $\alpha_v\beta_3$ integrin antigen. Then, an analysis of the affinity of the selected antibody based on the concentration was performed. The results are shown in FIG. 9 and Table 8.

As shown in FIG. 9 and Table 8, it was identified that the $K_D$ (Equilibrium dissociation constant) values of the VHH-13, VHH-22 and VHH-25 antibodies exhibited excellent $\alpha_v\beta_3$ integrin binding ability of 8.8 nM to 15.5 nM.

TABLE 8

| Analyte | Conc. | $K_a[M^{-1}s^{-1}]$ | $K_d[s^{-1}]$ | $K_D[M]$ |
|---|---|---|---|---|
| Integrin $\alpha_v\beta_3$ Ab | 0, 0.390625, 0.78125, 1.5625, 3.125, 6.25, 12.5, 25, 50 nM | 9.58(5)e4 | 1.6(3)e−5 | 166.9 ± 0.9 pM |
| Nanobody #13 | 0, 3.125, 6.25, 12.5, 25, 50, 100, 200, 400, 800 nM | 1.15(1)e5 | 0.001076(5) | 9.38 ± 0.08 nM |
| Nanobody #22 | 0, 3.125, 6.25, 12.5, 25, 50, 100, 200, 400, 800, 1600 nM | 6.27(3)e4 | 97.4(3)e−4 | 15.53 ± 0.07 nM |
| Nanobody #25 | 0, 3.125, 6.25, 12.5, 25, 50, 100, 200, 400, 800, nM | 9.86(4)e4 | 8.71(2)e−4 | 8.83 ± 0.04 nM |
| Nanobody #25-Lys | 0, 1.5625, 3.125, 6.25, 12.5, 25, 50, 100, 200, 400, 500 nM | 1.730(6)e5 | 8.02(2)e4 | 4.64 ± 0.02 nM |

<Example 7> Expression of Single-Domain Antibodies VHH-13, VHH-22 and VHH-25 According to the Present Disclosure In the Example 6, it was finally identified that VHH-13, VHH-22, and VHH-25 were the best among single-domain antibody clones according to the present disclosure. Thus, a vector to produce them was constructed and introduced into *E. coli*, thereby to express the single-domain antibody VHH-25.

Specifically, a vector containing a His6 tag was constructed for expression of VHH-13, VHH-22 or VHH-25, which are single-domain antibody clones selected according to the present disclosure. The vector map for VHH-25 (pALT-Avb3 VHH25) is shown in FIG. 10A. Further, in order to increase the binding strength to other functional molecules or elements, a vector containing Lysin and His6 tags was prepared, and a vector map (pALT-Avb3 VHH25K1) thereof is shown in FIG. 10B. The amino acid sequences containing His6 tag in clones VHH-25. VHH-13 and VHH-22 are represented by SEQ ID NOs: 14, 15 and 16, respectively.

The expression results of VHH-13, VHH-22 or VHH-25 containing the His6 tag were identified by performing reduced SDS-PAGE. The results are shown in FIG. 11A to FIG. 11C. The expression results of VHH-25 containing Lysin and His6 tags are shown in FIG. 11D.

As a result, VHH-13 was identified to have about 15.9 kDa (FIG. 11A), and VHH-22 was identified to have about 14.1 kDa (FIG. 11B). Further, it was identified that VHH-25 had about 14.5 kDa (FIG. 11C), and lysine-containing VHH-25 had about 14.2 kDa (FIG. 11D).

<Example 8> Identification of $\alpha_v\beta_3$ Integrin Targeting Effect of Single-Domain Antibody VHH-25 According to the Present Disclosure in Cancer Cells In order to identify the $\alpha_v\beta_3$ integrin targeting effect of the single-domain antibody VHH-25 according to the present disclosure in cancer cells in vitro, the following experiment was performed.

Specifically, 0.5 mg of VHH-25-K1 containing lysine and 0.25 mg of Cy5.5 (sulfo-Cy5.5-NHS, Lumiprobe) were dissolved in 2 ml of borate buffer (pH 8.4) and reaction occurred for 30 minutes at room temperature. After the reaction was completed, the Cy5.5-introduced antibody VHH-25-K was purified using a PD-10 column (GE healthcare). The results are shown in FIG. 12.

As shown in FIG. 12, the synthesis and purification of the Cy5.5-introduced antibody VHH-25-K was identified via SDS-PAGE. It was identified that $\alpha_v\beta_3$ integrin was selectively intracellularly untaken in activated U87-MG cells (human glioblastoma).

<Example 9> Identification of $\alpha_v\beta_3$ Integrin Targeting Effect of Single-Domain Antibody VHH-25 According to the Present Disclosure in Tumor Site In order to identify the $\alpha_v\beta_3$ integrin targeting effect of the single-domain antibody VHH-25 according to the present disclosure in a tumor mouse animal model, the following experiment was performed.

Specifically, an animal model was produced by inoculating U87-MG cells into Athymic nude mice (female, 6 to 8 weeks old). When the tumor was grown to a size of 0.8 cm to 1 cm, Cy5.5 was bound to VHH-25-K which in turn was injected into the tail vein (1 mg/kg). The contrast effect was analyzed using IVIS (PerkinElmer) over time. The results are shown in FIG. 13.

As shown in FIG. 13, from 30 minutes after the injection, the contrast effect may be identified at the tumor site. It was identified that the contrast signal appeared strongly for 4 hours. Then, it was identified that a continuous contrast signal appeared at the tumor site for 24 hours.

<Example 10> Identification of $\alpha_v\beta_3$ Integrin Targeting Effect of Single-Domain Antibody VHH-25 According to the Present Disclosure in Atherosclerosis Site In order to identify the $\alpha_v\beta_3$ integrin targeting effect of the single-domain antibody VHH-25 according to the present disclosure in an atherosclerotic mouse animal model, the following experiment was performed.

Specifically, an animal model in which intravascular plaques are formed is produced by performing a high fat diet in ApoE-/- mice (Female, 10 weeks old) for 36 weeks. Thereafter, Cy5.5 was conjugated to VHH-25-K as prepared in the same manner as in Example 9, which in turn was injected into the tail vein (1 mg/kg), and 4 hours later, the mice were sacrificed and the aorta was separated therefrom. The contrast effect of the isolated aorta was analyzed using IVIS. The results are shown in FIG. 14.

As shown in FIG. 14, it was identified that on 4 hours after the injection, a selective contrast effect appeared in the area where the plaque was formed.

The invention claimed is:

1. An $α_vβ_3$ integrin targeting single-domain antibody encoded by at least one selected from a group consisting of base sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

2. The $α_vβ_3$ integrin targeting single-domain antibody of claim 1, wherein the base sequence of SEQ ID NO: 1 encodes an amino acid sequence of SEQ ID NO: 11,
a base sequence of SEQ ID NO: 2 encodes an amino acid sequence of SEQ ID NO: 12, and
a base sequence of SEQ ID NO: 3 encodes an amino acid sequence of SEQ ID NO: 13.

3. The avß3 integrin targeting single-domain antibody of claim 1, wherein the antibody is a variable region of a heavy chain antibody (VHH) derived from Camelidae.

4. The $α_vβ_3$ integrin targeting single-domain antibody of claim 1, wherein a functional molecule or element is additionally bound to the antibody.

5. The $α_vβ_3$ integrin targeting single-domain antibody of claim 1, wherein a functional molecule or element is at least one selected from the group consisting of inorganic particles, radioactive isotopes, chemicals, peptides, polypeptides, nucleic acids, carbohydrates and lipids.

6. The $α_vβ_3$ integrin targeting single-domain antibody of claim 5, wherein the inorganic particles is fluorescent labels or dyes.

7. The $α_vβ_3$ integrin targeting single-domain antibody of claim 6, wherein the fluorescent labels or dyes are at least one selected from the group consisting of GFP (Green Fluorescent Protein), YFP (Yellow Fluorescent Protein), BFP (Blue fluorescent protein), CFP (Cyan fluorescent protein), Acridine dyes, Cyanine dyes, fluorone dyes, oxazine dyes, phenanthridine dyes, and rhodamine dyes.

8. The $α_vβ_3$ integrin targeting single-domain antibody of claim 5, wherein the radioactive isotopes are at least one selected from a group consisting of $^{18}F$ (fluorine), $^{11}C$ (carbon), $^{15}O$ (oxygen), $^{13}N$ (nitrogen), $^{89}Zr$ (zirconium), $C^{15}O$, $^{13}N$ (ammonia), $H_2^{15}O$, and $^{18}FDG$ (F-Deoxy Glucose).

9. A recombinant vector containing at least one selected from a group consisting of base sequences represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

10. A recombinant microorganism transformed with the recombinant vector of claim 9.

11. A composition for detecting angiogenesis, the composition includes the single-domain antibody of claim 1.

12. A kit for detecting angiogenesis, the kit includes the single-domain antibody of claim 1.

13. A composition for diagnosing angiogenesis-related diseases, the composition includes the single-domain antibody of claim 1.

14. The composition for diagnosing angiogenesis-related diseases of claim 13, wherein the angiogenesis-related disease is at least one selected from the group consisting of arteriosclerosis, cancer, diabetic retinopathy, angiogenesis glaucoma, posterior lens fibrosis, proliferative vitreous retinopathy, immature retinopathy, ophthalmic inflammation, corneal ulcer, conical cornea, macular degeneration, Sjogren's syndrome, myopia eye tumor, corneal graft rejection, abnormal wound union, trachoma, bone disease, rheumatoid arthritis, osteoarthritis, septicemia arthritis, hemangiomas, angiofibroma, psoriasis, pyogenic granuloma, proteinuria, abdominal aortic aneurysm disease, degenerative cartilage loss due to traumatic joint damage, neuro demyelination disease, liver cirrhosis, glomerular disease, immature rupture of the embryonic membrane, inflammatory bowel disease, periodontal ligament disease, restenosis, inflammation of the central nervous system, Alzheimer's disease, skin aging, thyroid hyperplasia, and Grave's disease.

15. A method for preparing an $α_vβ_3$ integrin targeting single-domain antibody, the method comprising:
(1) culturing a recombinant microorganism transformed with a recombinant vector containing at least one selected from a group consisting of base sequences represented by SEQ ID NO: 1, SEQ ID NO: 2, SEQ ID NO: 3, SEQ ID NO: 4, SEQ ID NO: 5, SEQ ID NO: 6, SEQ ID NO: 7 SEQ ID NO: 8, SEQ ID NO: 9 and SEQ ID NO: 10; and
(2) expressing a single-domain antibody for $α_vβ_3$ integrin in the microorganism.

* * * * *